US005942395A

United States Patent [19]
Fournier et al.

[11] Patent Number: 5,942,395
[45] Date of Patent: Aug. 24, 1999

[54] HYBRID RIBOZYMES AND METHODS OF USE

[75] Inventors: Maurille J. Fournier, Amherst; Dmitry A. Samarsky, Worcester, both of Mass.; Gerardo Ferbeyre; Robert Cedergren, both of Montreal, Canada

[73] Assignees: Universite de Montreal, Montreal, Canada; University of Massachusetts, Boston, Mass.

[21] Appl. No.: 08/853,217

[22] Filed: May 9, 1997

[51] Int. Cl.$^6$ .............................. C12Q 1/68; C12N 15/63; C12N 15/85; C07H 21/04
[52] U.S. Cl. ......................... 435/6; 435/91.1; 435/254.1; 435/320.1; 435/325; 435/366; 536/23.1; 536/24.5
[58] Field of Search .................................. 514/44; 435/6, 435/320.1, 325, 254.1, 366, 91.1; 536/23.1, 24.5

[56] References Cited

U.S. PATENT DOCUMENTS 5,494,814  2/1996  Haseloff et al. ..................... 435/172.3

FOREIGN PATENT DOCUMENTS

WO 92/01786  2/1992  WIPO .
WO 92/06988  4/1992  WIPO .
WO 93/15187  8/1993  WIPO .
WO 94/02595  2/1994  WIPO .
WO 94/17792  8/1994  WIPO .
WO 95/29241  11/1995  WIPO .
WO 95/30747  11/1995  WIPO .

OTHER PUBLICATIONS

Rojanasakul, Antisense oligonucleotide therapeutics: drug delivery and targeting. Advanced Drug Delivery Reviews, vol. 18, pp. 115–131, 1996.

Gewirtz et al., Facilitating oligonucleotide delivery: Helping antisense deliver on its promise, Proc. Natl. Acad. Sci., vol. 93, pp. 3161–3163, Apr. 1996.

Branch, A good antisense is hard to find, TIBS, vol. 23, pp. 45–50, Feb. 1998.

Balakin et al., The RNA world of the nucleolus: two major families of small RNAs defined by different box elements with related functions, Cell, vol. 86, pp. 823–834, Sep. 6, 1996.

A.G. Balakin et al., "*Saccharomyces cerevisiae* U14 Small Nuclear RNA Has Little Secondary Structure and Appears . . . Post–Transcriptional Processing", The Journal of Biological Chem. 269:739–746, 1994.

A.G. Balakin et al., "The RNA World of the Nucleolus: Two Major Families of Small RNAs Defined by Different Box . . . Related Functions", Cell 86:823–834, 1996.

E. Caffarelli et al., "Processing of the Intro–Encoded U16 and U18 snoRNAs: The Conserved C and D Boxes Control Both the Processing . . . of the Mature snoRNA", The EMBO Journal 15(5):1121–1131, 1996.

J. Cavaille et al., "Processing of Fibrillarin–Associated snoRNAs from pre–mRNA Introns: An Exonucleolytic Process . . . Stem–Box Terminal Structure", Biochimie 78:443–456, 1996.

A.C. Forster et al., Self–Cleavage of Virusoid RNA is Performed by the Proposed 55–Nucleotide Active Site Cell 50:9–16, 1987.

P. Ganot et al., "The family of box ACA small nucleolar RNAs is defined by an evolutionarily conserved . . . " Genes & Development, 11:941–956, 1997.

T. Hagervall et al., "Role of tRNA Modification in Translational Fidelity", Biochimica et Biophysica Acta, 1050:263–266, 1990.

Toinette Hartshorne et al., "A Common Core Structure for U3 Small Nucleolar RNAs", Nucleic Acids Research 22(16):3354–3364, 1994.

J. Haseloff et al., "Simple RNA Enzymes with New and Highly Specific Endoribonuclease Activities", Nature 334:585–591, 1988.

G.M. Huang et al., "Accumulation of U14 Small Nuclear RNA in *Saccharomyces cerevisiae* Requires Box C, Box D, and a 5', 3' Terminal Stem", Molecular and Cellular Biology 12(10):4456–4463, 1992.

Artur Jarmolowski et al., "Identification of Essential Elements in U14 RNA of *Saccharomyces Cerevisiae*", The EMBO Journal 9(13):4503–4509, 1990.

Z. Kiss–Laszlo et al., "Site–Specific Ribose Methylation of Preribosomal RNA: A Novel Function for Small Nucleolar RNAs", Cell 85:1077–1088, 1996.

B.A. Peculis et al., "Sequence and Structural Elements Critical for U8 snRNP Function in Xenopus Oocytes are Evolutionarily Conserved", Genes & Development 8:2241–2255, 1994.

D.E. Ruffner et al., "Sequence Requirements of the Hammerhead RNA Self–Cleavage Reaction", Biochemistry 29:10695–10702, 1990.

Michael P. Terns et al., "A Common Maturation Pathway for Small Nucleolar RNAs", The EMBO Journal 14(19): 4860–4871, 1995.

H. Tsui et al., "Absense of hisT–Mediated tRNA Pseudouridylation Results . . ." J.Bacteriology 173:7395–7400, 1991.

(List continued on next page.)

*Primary Examiner*—George C. Elliott
*Assistant Examiner*—Andrew Wang
*Attorney, Agent, or Firm*—Fish & Richardson P.C.

[57] ABSTRACT

New hybrid ribozymes that exhibit the high metabolic stability of small nucleolar ribonucleic acids (snoRNAs), and that cleave target sequences with high efficiencies in either cis (intra-molecular) or trans (inter-molecular) configuration are described. The hybrid ribozymes include (i) a ribozyme catalytic sequence; and (ii) a snoRNA stabilizing motif; wherein the catalytic sequence and the stabilizing motif are arranged to provide the RNA molecule with a three-dimensional configuration in which the catalytic sequence is positioned to interact with a target sequence and the stabilizing motif adopts a conformation that stabilizes the RNA molecule, and additionally enables the RNA molecule to localize in the nucleolus of a cell.

26 Claims, 9 Drawing Sheets

OTHER PUBLICATIONS

K. Tyc et al., "U3, U8 and U13 Comprise a New Class of Mammalian snRNPs Localized in the Cell Nucleolus", The EMBO Journal 8(10):3113–3119, 1989.

O.C. Uhlenbeck, "A Small Catalytic Oligoribonucleotide", Nature 328:596–600, 1987.

N.J. Watkins et al., "Elements Essential for Processing Intronic U14 snoRNA are Located at the Termini of the Mature SnoRNA . . . Nucleotide Boxes C and D", RNA 2:118–133, 1996.

L. Xia et al., "Identification of Specific Nucleotide Sequences and Structural Elements Required for Intronic U14 snoRNA Processing", RNA 3:17–26, 1997.

HYBRID RIBOZYMES AND METHODS OF USE

STATEMENT AS TO FEDERALLY SPONSORED RESEARCH

This invention was funded in part by National Institutes of Health Grant No. GM 19351. The government may have certain rights in the invention.

FIELD OF THE INVENTION

The invention relates to enzymatic ribonucleic acid ("RNA") molecules called ribozymes.

BACKGROUND OF THE INVENTION

Ribozymes are RNA molecules that are capable of performing various biochemical reactions. The best characterized ribozymes are those that provide site-specific cleavage of the sugar-phosphate backbone in RNAs. Naturally occurring ribozymes generally cleave RNA targets in cis, whereas artificial ribozymes have been designed to cut substrate molecules in both cis and trans configuration (Cech, *Curr. Opin. Struct. Biol.*, 2:605–609, 1992).

Ribozyme-mediated RNA cleavage has been extensively studied in vitro (Uhlenbeck, *Nature*, 328:596–600, 1987; Haseloff et al., *Nature*, 334:585–591, 1988; Hampel et al., *Nucleic Acids Res.*, 18:299–304, 1990). Small ribozymes have been demonstrated to cleave substrate molecules in trans with high efficiency. However, in vivo experiments have revealed important fundamental differences between the test tube and living cells, and the ability to utilize ribozymes in vivo is far from its full potential (e.g., Sarver et al., *Science*, 247:1222–1225, 1990; Ojwang et al., *Proc. Natl. Acad. Sci. USA*, 89:10802–10805, 1992; Ferbeyre et al., *J. Biol. Chem.*, 271:19318–19323, 1996). Despite many examples of ribozyme-dependent inhibition of gene expression in different organisms, better ribozymes and ribozyme strategies are needed for in vivo applications.

Factors that limit ribozyme activity in vivo have been partially characterized. They include difficulties in: (1) providing sufficiently high levels of ribozymes due often to metabolic instability; (2) predicting folding of the target and catalytic RNAs, which is essential as the catalytic and target RNAs interact through exposed complementary sequences; (3) achieving co-localization of the ribozymes and target RNAs in the cell; and (4) predicting, and thus avoiding, undesirable RNA-RNA and/or RNA-protein interactions that interfere with the desired function.

SUMMARY OF THE INVENTION

The invention is based on the discovery that when a catalytic sequence of a ribozyme is combined with certain structural elements of a small nucleolar RNA ("snoRNA"), the resultant new RNA molecule, a so-called "hybrid ribozyme," exhibits the high metabolic stability of a snoRNA, and cleaves target sequences with high efficiencies in either cis (intra-molecular) or trans (inter-molecular) configuration.

Accordingly, the invention features recombinant RNA molecules, i.e., hybrid ribozymes, that include (i) a ribozyme catalytic sequence, e.g., a hammerhead ribozyme or hairpin ribozyme catalytic sequence; and (ii) a small nucleolar RNA (snoRNA) stabilizing motif; wherein the catalytic sequence and the stabilizing motif are arranged to provide the RNA molecule with a three-dimensional configuration in which the catalytic sequence is positioned to interact with a target sequence, and the stabilizing motif adopts a conformation that stabilizes the RNA molecule, and additionally enables the RNA molecule to localize in the nucleolus of a cell. The hybrid ribozyme has a higher metabolic stability than its cognate ribozyme.

A "ribozyme catalytic sequence" is an RNA sequence, or group of RNA sequences, that is identical to a catalytic sequence from any natural or artificial ribozyme, and cleaves a target nucleic acid sequence with the same efficacy as the catalytic sequence from the ribozyme. A catalytic sequence in a natural or artificial ribozyme is a sequence, or group of sequences, that forms the catalytic domain of the ribozyme and effects the enzymatic function of the ribozyme, but does not directly define the ribozyme's substrate specificity (e.g., by base pairing with the substrate). For instance, the catalytic sequence of a classic hammerhead ribozyme consists of three discrete segments (i.e., those forming the central core motif, which is the catalytic domain) separated by structural or targeting sequences (i.e., those forming the three helical arms). A ribozyme catalytic sequence can be, for example, tested in the target cleavage assay described below. Hammerhead and hairpin ribozymes are of particular interest here due to their small size and relatively simple structural elements.

A "snoRNA stabilizing motif" is a ribonucleic acid sequence or group of two or more ribonucleic acid sequences, that automatically adopts a particular three-dimensional configuration in vivo (or in a liquid medium in vitro) that is substantially identical to the three-dimensional configuration of a structural element or group of structural elements from any natural or artificial snoRNA that, by binding to proteins and/or other biological compounds (e.g, other nucleic acids), protect the snoRNA from degradation in vivo (thus allowing the snoRNA to accumulate). The stabilizing motif can be additionally able to localize the snoRNA in the nucleolus of a cell. A snoRNA stabilizing sequence can be tested in the nucleolus localization and stability assays described below.

The snoRNAs whose structural elements are chosen as the stabilizing sequences can be from any eukaryotic cells (e.g., yeast cells, animal cells, and plant cells). Examples of snoRNA structural elements that result in metabolic stability and/or nucleolar localization include, but are not limited to, the so-called box C(C') and D(D') elements found in one family of snoRNAs, ACA box, and H box elements found in a second family of snoRNAs, and 5' trimethylguanosine caps found in many non-intronic snoRNAs (Peculis et al., *Genes. Dev.*, 8:2241–2255, 1994).

Accordingly, the stabilizing motif can be a box C(C') sequence and a box D(D') sequence. For example, the box C(C') sequence can have the sequence DGAHBN, wherein D is U, G, or A; H is U, A, or C; B is G, U, or C; and N is any ribonucleotide, e.g., the sequence UGAUGA. The box D sequence can be the sequence NYVWGA, where N can be any ribonucleotide; Y is either C or U; V is C, G, or A; and W is U or A, e.g., the sequence GUCUGA.

Box C(C') and box D(D') elements are short nucleotide sequences (e.g., 4 to 6 nucleotides) that have been identified in a variety of snoRNAs, for example as described in Maxwell et al., *Ann. Rev. Biochem.*, 35:897–934 (1995); Xia et al., *RNA*, 3:17–26 (1997); and Watkins et al., *RNA*, 2:118–133 (1996). As used herein, the terms box C, box C', and box C(C'), are used interchangeably, and refer to the structural elements of snoRNAs as described in Maxwell et al., 1995. Likewise, D and D' are used interchangeably.

The RNA molecule can further include a helical stem, wherein the helical stem includes a first flanking sequence located adjacent and within four nucleotides of the box C(C') sequence, and a second flanking sequence located adjacent and within four nucleotides of the box D sequence, and wherein the first and second flanking sequences are complementary to each other and each include four or more nucleotides. For example, the first flanking sequence can include the sequence UUCA, and the second flanking sequence can include the sequence UGAA. Further, the first flanking sequence can be positioned within two nucleotides of the box C(C') sequence, and the second flanking sequence can be positioned within two nucleotides of the box D sequence.

In other embodiments, the stabilizing motif can be a 5' trimethylguanosine cap or an ACA box and an H box. The ACA box is a three nucleotide sequence (i.e, ACA; or active variants thereof, such as AUA and ACA) identified in a variety of snoRNAs that lack boxes C and D, for example as described in Balakin et al., *Cell*, 86:823–834 (1996). The H box is found in the hinge region of ACA box snoRNAs, and has a consensus sequence of AnAnnA, n being any one of A, U, C, and G (Ganot et al., *Genes Dev.*, 11:941–956, 1997). Any of these structural elements used for constructing hybrid ribozymes can be either those found in naturally occurring snoRNAs or active variants thereof. Activity of variant elements can be tested using the assays described below.

In another embodiment, the invention includes hybrid ribozymes that further comprise a target sequence that is cleaved by the ribozyme catalytic sequence. The target sequence can flank the catalytic sequence or can be brought into steric proximity with the catalytic sequence during folding of the hybrid ribozyme. In some cases, the catalytic sequence and the target sequence are embedded within each other, and thus need not be two distinct entities. These are cis-acting hybrid ribozymes.

In alternative embodiments, the target sequences do not reside within the hybrid ribozymes themselves. Instead, recognition sequences complementary to the target sequences, or segments thereof, are incorporated into the hybrid ribozyme so that it can be directed to its substrate by these recognition sequences. These hybrid ribozymes are trans-acting. The region of complementarity can contain gaps or non-Watson-Crick base-pairing, provided that a sufficient base-pairing interaction is maintained to permit the enzymatic reaction.

In another aspect, the invention features a eukaryotic expression vector including a first nucleic acid sequence encoding the new RNA molecules. The vector can further include a restriction enzyme site within the first nucleic acid sequence for inserting a second nucleic acid sequence encoding a target sequence, or a sequence complementary thereto, of the catalytic sequence.

The invention further features a pharmaceutical composition including the eukaryotic expression vector directing expression the new RNA molecules.

In another aspect, the invention features a method of modulating gene expression in a eukaryotic cell, by introducing one of the new RNA molecules into the cell.

The invention provides several advantages concomitantly. First, the new hybrid ribozymes can be accumulated in vivo. This feature is made possible by the snoRNAs's stabilizing elements incorporated into the hybrid ribozymes. By manipulating metabolic stability, the level of hybrid ribozyme accumulation can be altered in a graded fashion. Second, the new hybrid ribozymes can readily interact with their target sequences. This advantage is afforded by the use of structural elements of snoRNAs. Specifically, a target sequence (or a recognition sequence complementary to the target sequence) can be inserted in a region of the hybrid ribozyme analogous to a region of the snoRNA that is exposed and to interact with rRNA through complementary base pairing.

Third, one of the two cleavage products of cis-hybrid ribozymes remains linked to the snoRNA structural elements; the product is thereby stabilized and can be readily traced. This feature will greatly facilitate the in vivo studies of ribozymes. Further, since end(s) of this product are inevitably trimmed by exonucleases in vivo up to the point where the product is protected by a snoRNA-like core structure (e.g., the box C(C')/D motif), an in vivo cleavage product can be distinguished from a corresponding in vitro cleavage product by the former's smaller size. Thus, an authentic in vivo cleavage can be readily distinguished from a cleavage that may occur during in vitro handling (e.g., purification) of the cis-ribozyme.

Fourth, the present hybrid ribozymes can be transported to nucleoli due to the presence of the snoRNA structural elements. Thus, the ribozymes can be used to reliably target any nucleolar RNAs such as ribosomal RNAs or precursors thereof and the natural snoRNAs involved in ribosome biogenesis. Of course, since all nuclear-encoded, non-ribosomal RNAs are synthesized in the nucleoplasm, nascent hybrid ribozymes, when designed with the appropriate recognition sequences, can also target RNAs localized in the nucleoplasm (e.g., mRNAs, tRNAs, and nucleoplasmic snRNAs).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1A:
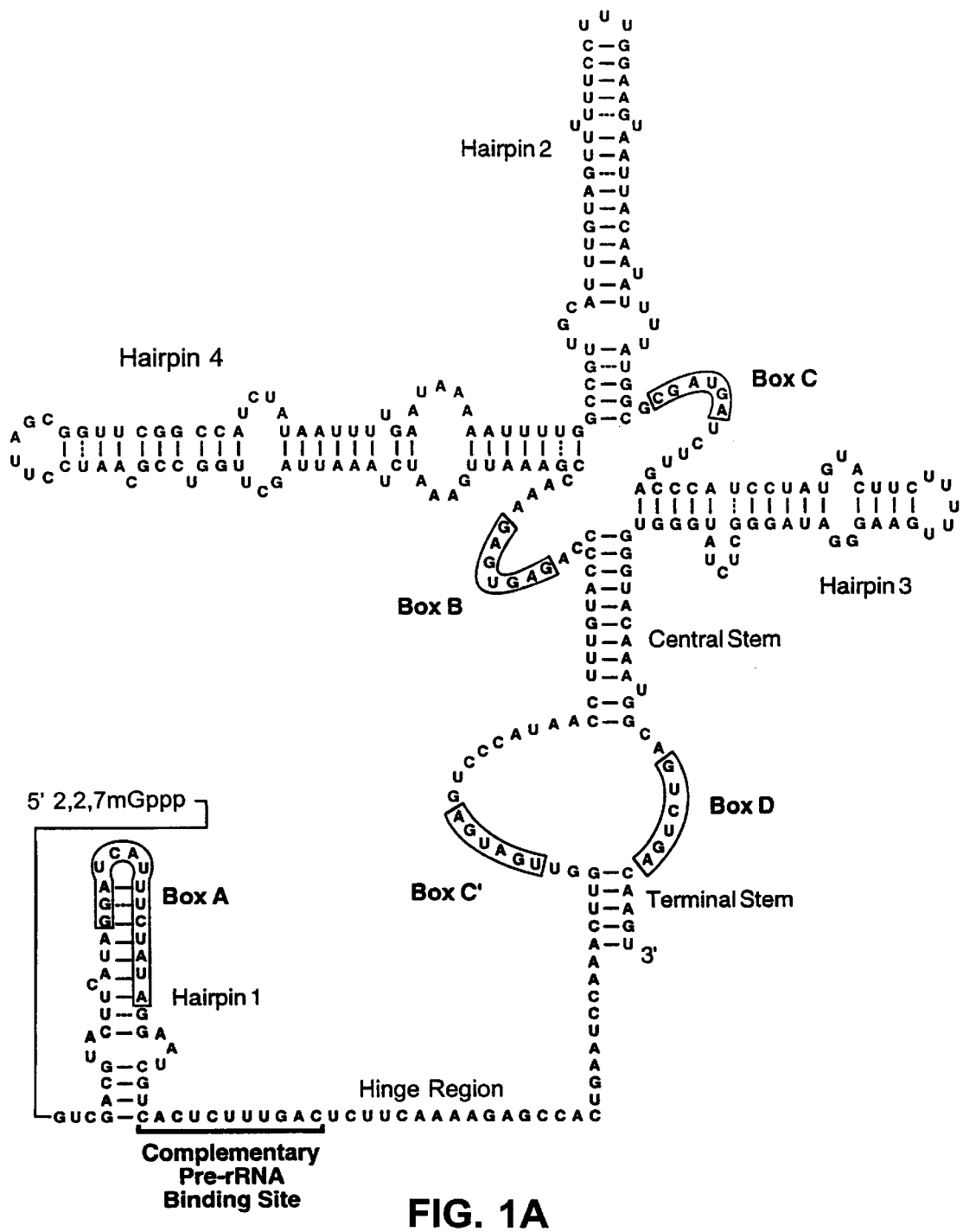
FIG. 1A is a functional map of *S. cerevisiae* U3 snoRNA (SEQ ID NO:29).
Figure 1B:
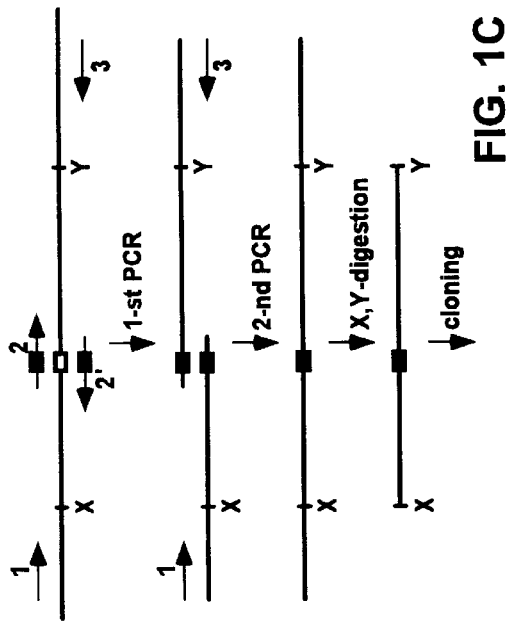
FIGS. 1B–1E are schematic diagrams showing various U3 mutagenesis strategies. The strategies can be selected based on the position and the length of the mutagenized sequence as well as on the number of sequences to be substituted.
Figure 1C:
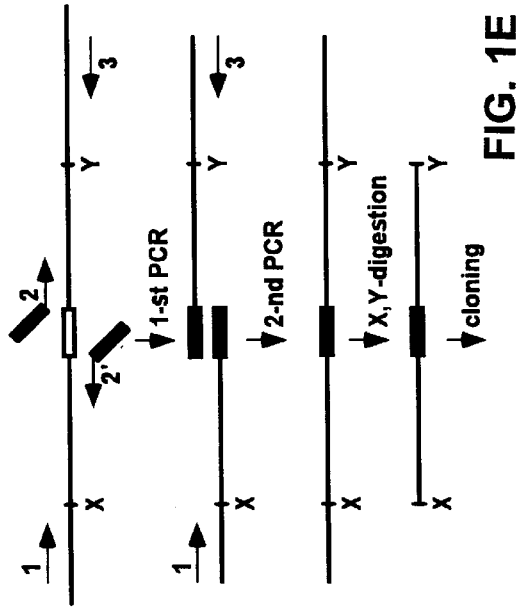
Figure 1D:
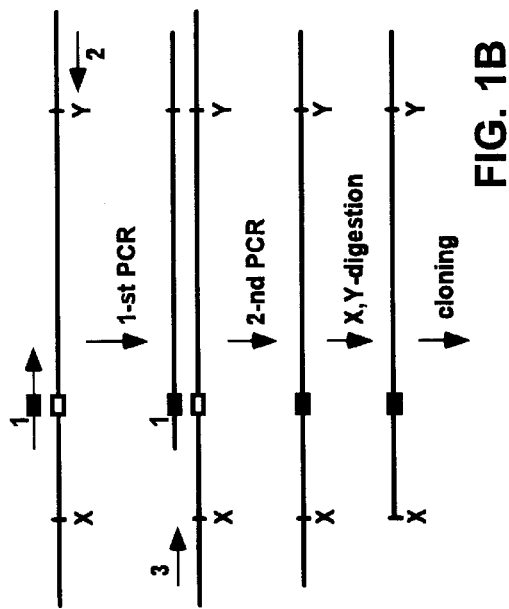
Figure 1E:
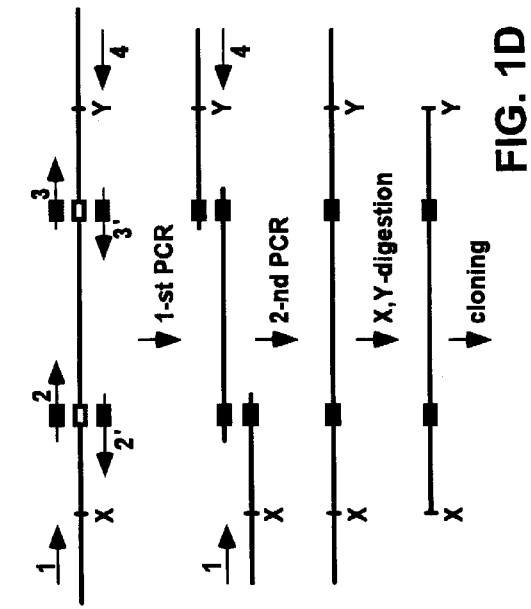

The basis of the invention is that certain structural elements of snoRNA can stabilize heterologous RNAs and can therefore be utilized, with or without additional heterologous sequences to generate hybrid ribozymes that have high metabolic stability and activity. Heterologous sequences are those that are not related to snoRNAs, or those that are present in the cognate snoRNAs but are not in the same relative position in the hybrid ribozymes as in the cognate snoRNAs. The new hybrid ribozymes display excellent stability, and are able to cleave specific target sequences with high (e.g., up to 60, 85, even 95 percent) efficiency in both cis and trans configurations.

Hybrid Ribozymes

The hybrid ribozymes contain a catalytic sequence derived from a ribozyme catalytic sequence, and a stabilizing motif derived from structural elements of a snoRNA, where the catalytic sequence is positioned in the hybrid ribozyme molecules such that it can interact with a target sequence and does not impair the stabilizing effect of the stabilizing motif. The new hybrid ribozymes can also include target and recognition sequences.

SnoRNA Stabilizing Motif

The stabilizing motif in the hybrid ribozymes are identical to portions or elements of snoRNAs (or active mutants thereof). snoRNAs are small RNAs found in the nucleoli of eukaryotic cells; these RNAs participate in ribosomal RNA ("rRNA") processing and site-specific modification of rRNA nucleotides.

Nearly all snoRNAs can be classified into two large families, i.e., the box C(C')/D family and the ACA box family, based on the presence of short conserved sequence elements (Maxwell et al., supra; Balakin et al., *Cell*, 86:823–834, 1996). Members of the box C(C')/D family include box C(C') and box D elements that are almost always near the 5' and 3' ends of the snoRNA molecules (Xia et al., *RNA*, 3:17–26, 1997, and Watkins et al., *RNA*, 2:118–133, 1996). The ACA box family members include an ACA triplet (or certain active variants) located three nucleotides upstream from the 3' terminus (Ganot et al., supra; Balakin et al., supra). MRP/7-2 snoRNA, a phylogenetically conserved snoRNA, does not belong to either family. This snoRNA is also involved in rRNA processing (Maxwell et al, *Ann. Rev. Biochem.*, 35:897–934, 1995).

Examples of stabilizing elements in snoRNAs include the box C(C')/D motifs found in box C(C')/D snoRNAs, the ACA box and the H box found in ACA box snoRNAs, and 5' trimethylguanosine (TMG) caps present in many non-intronic snoRNAs.

Boxes C(C') and D are conserved phylogenetically. Typically, they consist of UGAUGA and GUCUGA, respectively. While variations at most of the positions have been observed, the second and third nucleotides in box C (i.e., -GA---) and the last two nucleotides in box D (i.e., ----GA) appear to be most conserved. A large number of box C(C') and box D nucleotide sequences have been discovered and described. See, for example, Table 1 of Xia et al., 1997, which is incorporated herein by reference.

A general formula for box C(C') is D<u>GA</u>HBN, where D is U, G, or A; H is U, A, or C; B is G, U, or C; and N can be any ribonucleotide. A general formula for box D is NYVW<u>GA</u>, where N can be any ribonucleotide; Y is either C or U; V is C, G, or A; and W is U or A. Specific box C(C') sequences of human snoRNAs U3, U22, and U28 are <u>G</u>GA <u>A</u>GA, UGA<u>A</u>GA, and UGAU<u>U</u>U, respectively; while the box D sequences of human U8 and U24 are <u>A</u>UCUGA and <u>C</u>GCUGA, respectively (nucleotides different from the canonical ones are underlined).

Despite the sequence variations, it has been demonstrated that many of the box C(C') sequences or box D sequences are interchangeable. Notably, in nearly all of the box C(C')/D snoRNAs studied so far (e.g., U14 and U3), the boxes C(C') and D are brought into close proximity by either the base-pairing between their distal flanking sequences (see, e.g., Example 1, infra, and the terminal stem of U3 in FIG. 1; Balakin et al. supra) and/or their proximal flanking sequences (e.g., the central stem of U3 in FIG. 1). The two boxes can also be brought into proximity by interaction (e.g., base-pairing or other mechanisms) between non-coding sequences on the precursor of the snoRNA.

Accordingly, the hybrid ribozymes can include flanking sequences that form a helical stem, and each include, for example, from 3 to about 6 nucleotides. These flanking sequences are located, for example, adjacent to and within 0 to about 4 nucleotides of the box C(C') or box D sequences, and are complementary to each other. The flanking sequences can be positioned on the 3' or 5' end of their respective box sequence. The flanking sequences can contain any combination of nucleotides, as long as they are complementary to each other. These flanking sequences can even contain deoxyribonucleotides, provided that they can form the helical stem structure.

In addition to naturally occurring box C(C') and D sequences, variants of these sequences can also be used to generate the new hybrid ribozymes, provided that these variants form the same type of conformation in the hybrid ribozymes as would the naturally occurring box C(C') and D sequences. The Examples below provide guidance as to how variants of the box C and D motifs or other snoRNA structural elements can be tested for functionality.

The boxes C(C') and D are generally arranged in the same relative orientation in the hybrid ribozymes as in canonical box C(C')/D snoRNAs, i.e., 5'-$N_a$-BOX C(C')-$N_b$-BOX D-$N_c$-3'; where N is any ribonucleotide; and a, b, and c are the number of ribonucleotides flanking the boxes C and D. Other orientations can also be adopted, as long as these orientations retain the metabolism-stabilizing effects of these elements, which effects can be readily determined based on the examples below. The catalyzing sequence can be positioned within $N_a$, $N_b$, or $N_c$, as long as the catalytic sequence does not interfere with the three-dimensional configuration and thus the stabilizing effects of the box C(C')/D motif.

The stabilizing effects of snoRNA elements can be readily determined using techniques well known in the art, for example as described in Huang et al., *Mol. Cell. Biol.*, 12:4456–4463 (1992). For instance, a test RNA containing a specific snoRNA stabilizing motif, such as box C and box D elements, or a TMG cap, can be extracted from cells expressing this test RNA and examined by Northern blot analysis. The integrity of the test RNA is indicated by its size, as revealed by a labeled probe. A control is a test RNA that does not include the stabilizing motif.

Localization can be analyzed by: (i) standard cell fractionation procedures such as differential centrifugation (e.g., to isolate nucleoli); or (ii) demonstrated association with known nucleolar components (such as the protein fibrillarin), typically using immunoprecipitation procedures; and (iii) in situ hybridization, typically with fluorescent probes and epifluorescent microscopy (see, e.g., Long et al., *RNA*, 1:1071–1078 (1995).

Ribozyme Catalytic Sequences

Catalytic sequences from any ribozyme can be used to prepare the new hybrid ribozymes. Small ribozymes (e.g., endonucleolytic hammerhead and hairpin ribozymes) are particularly useful, as they impose fewer steric requirements in the hybrid products. Additional ribozymes that can be used include, but are not limited to, other nucleolytic ribozymes (e.g., group I and II introns, RNaseP, VS, leadzyme, or hepatitis δ virus ribozyme) as well as ribozymes that are RNA ligases (Bartel et al., *Science*, 261:721–729, 1993), polynucleotide kinases (Lorch et al., *Nature*, 374:777–782, 1995), or aminoacyl synthases (Illangasekare et al., *Science*, 267:643–647, 1995).

In general, the catalytic sequences are arranged in the hybrid ribozymes such that they can readily interact with their targets. In addition, the catalytic sequences are positioned so that they do not sterically interfere with the stabilizing sequence, e.g., the sequence that can form the box C/D-stem structure described above.

Specifically, the catalytic sequence can be inserted into regions of the hybrid ribozymes that are analogous to exposed regions (e.g., regions that are known to interact with rRNA targets) of the cognate snoRNA. For instance, the 5' single-stranded hinge region of U3 snoRNA (see FIG. 1A) can interact with rRNA. Thus, if the stabilizing sequence is derived from U3, the catalytic sequence can be inserted into a region corresponding to the 5' hinge region of the cognate U3.

Certain non-essential nucleotides in the ribozyme catalytic sequence can be changed, for example, to introduce convenient cloning sites. These non-essential nucleotides can be determined by mutation analysis, as described herein.

The catalytic sequence in a ribozyme can be determined by well-known methods, such as those used for determining the structure and the catalytic sequences of hammerhead ribozymes. For instance, mutation analysis can be used to determine which nucleotides in a ribozyme are essential for its catalytic function. These methods are described below (see, e.g., Example 1).

Target and Recognition Sequences

The invention provides two types of hybrid ribozymes, i.e., cis-acting ribozymes, in which target sequences are part of the ribozymes, and trans-acting ribozymes, in which target sequences are not part of the ribozymes.

In cis-acting hybrid ribozymes, the target sequences are arranged in such a way that they are accessible to the catalytic domain formed by the catalytic sequence. The catalytic sequence and the target sequence are sometimes not two separate entities; but if they are, they can be placed in the same relative positions in the hybrid ribozymes as in ribozymes in which identical catalytic and target sequences are located.

Trans-acting hybrid ribozymes contain no target sequences; however, recognition sequences that interact (e.g., through base-pairing or other non-covalent bonds or transient covalent bonds) with the target sequences can be incorporated into the hybrid ribozymes, e.g., into, or adjacent to, the catalytic sequences, to define the substrate-specificity of the hybrid ribozymes. For instance, a classic hammerhead ribozyme and its substrate (either cis or trans) form a secondary structure consisting of three helices joined at a central core of 11 to 12 single-stranded nucleotides (Ruffner et al., *Biochemistry*, 29:10695–10702, 1990, and references therein). By changing the nucleotides of the regions of the ribozyme that form helices with the substrate, the specificity of the ribozyme can be changed accordingly. Any equivalent sequences that are part of the catalytic sequence can be altered similarly to endow the catalytic sequence with new substrate specificity.

Methods for Generating Hybrid Ribozymes

The present hybrid ribozymes can be expressed, in vitro or in vivo (e.g., in target cells), from nucleic acids encoding them. Expression constructs encoding hybrid ribozymes can be generated using standard molecular cloning techniques (see, e.g., Sambrook et al., *Molecular Cloning, A Laboratory Manual*, 2nd Ed., Cold Spring Harbor Laboratory Press, Cold Spring Harbor, New York, 1989; WO 92/01786; and Ausubel et al., *Current Protocols in Molecular Biology*, Greene Publishing and Wiley-Interscience, New York, N.Y., 1993).

The expression constructs generally contain a ribozyme-encoding nucleic acid molecule operably linked to a proper transcriptional regulating sequence (e.g., a promoter and optionally an enhancer). The expression constructs can be made with an autonomously replicating plasmid or viral vector, or can be integrated into the host genome. Any vector that can transfect a target cell can be used in the invention. Preferred vectors are viral vectors, including those derived from retroviruses (see, e.g., WO89/07136; Rosenberg et al., N. Eng. J. Med., 323(9):570–578, 1990), adenovirus (see, e.g., Morsey et al., J. Cell. Biochem., Supp. 17E, 1993; Graham et al., at 109–128, Vol. 7, in Murray, ed., Methods in Molecular Biology: Gene Transfer and Expression Protocols, Clifton, N.J., Human Press 1991), adeno-associated virus (Kotin et al., Proc. Natl. Acad. Sci., USA, 87:2211–2215, 1990), replication defective herpes simplex viruses (HSV; Lu et al., Abstract, page 66, Abstracts of the Meeting on Gene Therapy, Sep. 22–26, 1992, Cold Spring Harbor Laboratory, Cold Spring Harbor, N.Y.), replication-defective hepatitis viruses (e.g., HBV and HCV), and any modified versions of these vectors. Retroviral vectors are particularly useful if the target cells are cancer cells, since these vectors are selectively integrated into fast-growing cells.

Any promoter that is capable of directing initiation of transcription in a eukaryotic cell can be used in the invention. For example, non-tissue specific promoters, such as the cytomegalovirus (DeBernardi et al., Proc. Natl. Acad. Sci. USA 88:9257–9261, 1991, and references therein), mouse metallothionine I gene (Hammer, et al., J. Mol. Appl. Gen. 1:273–288, 1982), HSV thymidine kinase (McKnight, Cell 31:355–365 1982), and SV40 early (Benoist et al., Nature 290:304–310, 1981) promoters can be used. Tissue-specific promoters can also be selected, depending on the type of cell in which expression of the hybrid ribozyme is desired. Viral promoters and enhancers, such as those from cytomegalovirus, herpes simplex viruses (types I and II), hepatitis viruses (A, B, and C), and Rous sarcoma virus (RSV; Fang et al., Hepatology 10:781–787, 1989), can also be used in the invention.

To obtain purified hybrid ribozymes, host cells can be transformed with appropriate expression constructs; and the expressed hybrid ribozymes can be extracted and purified using standard RNA purification techniques (see, e.g., Sambrook et al., supra; Ausubel et al., supra). Alternatively, the hybrid ribozymes can be chemically synthesized with standard techniques, or biochemically (enzymatically) synthesized using standard in vitro transcription methods.

Uses of the Hybrid Ribozymes

The new hybrid ribozymes can be localized to the nucleolus due to the presence of the snoRNA elements such as boxes C(C') and D. Therefore, the hybrid ribozymes, especially the trans-acting ribozymes, can target RNAs in the nucleolus (e.g., ribosomal RNAs or precursors thereof, and snoRNAs or precursors thereof), as well as RNAs in the nucleoplasm (e.g., messenger RNAs, small nuclear RNAs, transfer RNAs, and genomic RNAs of intracellular pathogens such as retroviruses) where all non-ribosomal RNAs, including the hybrid ribozymes, are initially transcribed.

These features allow the present hybrid ribozymes to be used to positively or negatively modulate expression of endogenous or exogenous genes. For example, to treat cancer, one can introduce into cancer cells hybrid ribozymes that cleave in a sequence-specific manner the mRNA(s) of an oncogenic polypeptide [e.g, ras, met, sis, erbB, abl, jun, fos, myc, or mdr (which is responsible for multidrug resistance to chemotherapy)], or the mRNA(s) of an inhibitor of a tumor-suppressor gene (e.g., Rb, p53, SV40 large T antigen, adenovirus E1A, and papillomavirus E5 and E7). Similarly, to treat other disease states (e.g., cardiovascular disease or autoimmune disease), one can administer to the diseased cells hybrid ribozymes of the invention or expression constructs thereof, targeting mRNAs specifically associated with these disease states.

To eradicate or inhibit the growth of intracellular pathogens, one can introduce into the infected cells a hybrid ribozyme that specifically cleaves the RNA genome of the pathogens or RNA transcribed from the genome of the pathogens. Examples of pathogens include, but are not limited to, viruses (e.g., human immunodeficiency virus, hepatitis A, B, or C virus, papilloma virus, herpes virus, or measles virus), bacteria (e.g., Corynebacterium diphtheria, Bordetella pertussis), and intracellular eukaryotic parasites (e.g., Plasmodium spp., Schistosoma spp., Leishmania spp., Trypanosoma spp., or Mycobacterium lepre).

Alternatively, to inhibit growth of undesired cells (e.g., cancer or infected cells, immune cells involved in inflammation or autoimmune disease, or fibroblasts involved in atherosclerosis), one can introduce into these cells hybrid ribozymes that interfere with the cells' general cellular metabolism (e.g., rRNA or snoRNA synthesis). To avoid side effects, it is preferred that the hybrid ribozyme is specifically targeted to the undesired cells, but not bystander cells (see below).

In addition, cis-acting hybrid ribozymes that are activated upon binding to target RNAs (e.g., mRNAs of genes associated with disease states) can be used for diagnostic purposes.

The new hybrid ribozymes can also be used to genetically modify agricultural and industrial eukaryotic organisms (non-human animals, plants and lower eukaryotes) with the goal of improving or achieving new performance properties. For instance, yeast strains used in wine and beer production are usually not amenable to conventional genetic methods useful in laboratory strains; thus, to establish yeast strains with improved fermenting properties, hybrid ribozymes that target certain undesirable genes can be stably integrated into appropriate yeast cells. Other industrial uses of the new hybrid ribozymes include, but are not limited to, creating auxotrophic fungal and plant strains that can be used to develop improved transformation systems, modifying fungi and plants used in production of recombinant proteins, and creating plants with improved resistance to pathogens.

In a further aspect, since different target or recognition sequences can be incorporated into the present hybrid ribozymes, the hybrid ribozymes specific for various substrates can be readily generated, facilitating the studies of RNA structure and function, including interaction of RNA with other natural or synthetic compounds (e.g, DNA, other RNA, or proteins) and RNA transportation. The new hybrid ribozymes can be used either in vivo or in vitro (e.g, in a cell-free or a protein-free system) for these and other purposes.

The hybrid ribozymes of the invention can be introduced into cells using standard gene therapy methods (see, e.g., WO 94/17792). For example, the hybrid ribozymes can be produced within a target cell by transcription of an expression construct (supra).

Recombinant nucleic acid sequences (e.g., expression constructs) encoding hybrid ribozymes can be used in therapeutic (or pharmaceutical) compositions for, e.g., treating conditions associated with undesired expression of an mRNA (e.g., to treat viral infections). The therapeutic compositions of the invention can be used alone or in admixture, or in chemical combination, with one or more materials, including other recombinant vectors, materials that increase the biological stability of the recombinant vectors, or materials that increase the ability of the therapeutic compositions to specifically penetrate the relevant cell type. The therapeutic compositions of the invention are administered in pharmaceutically acceptable carriers (e.g., physiological saline), which are selected on the basis of the mode and route of administration, and standard pharmaceutical practice. Suitable pharmaceutical carriers, as well as pharmaceutical necessities for use in pharmaceutical formulations, are described in *Remington's Pharmaceutical Sciences*, a standard reference text in this field, and in the USP/NF.

The therapeutic compositions of the invention are administered in dosages determined to be appropriate by one skilled in the art. An appropriate dosage is one that effects a desired result, e.g., a reduction in a symptom of a disease sought to be treated. It is expected that the dosages will vary, depending upon the pharmacokinetic and pharmacodynamic characteristics of the particular agent, and its mode and route of administration, as well as the age, weight, and health of the recipient; the nature and extent of any relevant disease; the frequency and duration of the treatment; the type of, if any, concurrent therapy; and the desired effect. It is expected that a useful dosage contains between about 0.1 to 100 mg of active ingredient per kilogram of body weight. Ordinarily, 0.5 to 50 mg, or 1 to 10 mg of active ingredient per kilogram of body weight per day given in divided doses, or in sustained release form, is appropriate.

The therapeutic compositions of the invention can be administered to a patient by any appropriate mode, e.g., parenterally, intraperitoneally, orally, topically (e.g., with dimethyl sulfoxide), or intravenously, as determined by one skilled in the art. Alternatively, it may by necessary to administer the compositions surgically to the target tissue. The treatments of the invention can be repeated as needed, as determined by one skilled in the art.

Any method that accomplishes in vivo transfer of nucleic acids into eukaryotic cells can be used. For example, hybrid ribozymes or expression constructs thereof can be packaged into liposomes, non-viral nucleic acid-based vectors, erythrocyte ghosts, or microspheres (e.g., microparticles; see, e.g., U.S. Pat. Nos. 4,789,734; and 4,925,673; 3,625,214; and Gregoriadis, *Drug Carriers in Biology and Medicine*, pp. 287–341 (Academic Press, 1979)). Further, delivery of expression constructs encoding hybrid ribozymes can be accomplished by direct injection into target tissues, for example, in a calcium phosphate precipitate or coupled with lipids.

Exogenously provided hybrid ribozymes can contain modified nucleotides, e.g., modified nucleotides that enhance stability. For example, the hybrid ribozymes can contain inter-nucleotide linkages other than phosphodiester bonds, such as phosphorothioate, methylphosphonate, methylphosphodiester, phosphorodithioate, phosphoramidate, phosphotriester, or phosphate ester linkages (Uhlman et al., *Chem. Rev.* 90(4):544–584, 1990; Tidd et al., *Anticancer Research* 10:1169, 1990). Hybrid ribozymes' stability can also be increased by incorporating 3'-deoxythymidine or 2'-substituted nucleotides (substituted with, e.g., alkyl groups) into the ribozymes during synthesis, by providing the ribozymes as phenylisourea derivatives, or by having other molecules, such as aminoacridine or polylysine, linked to the 3' ends of the snoRNAs (see, e.g., Tidd et al, *Anticancer Research* 10:1169–1182, 1990). Modifications of the RNA nucleotides of the hybrid ribozymes of the invention may be present throughout the ribozymes, or in selected regions, e.g., the 5' and/or 3' ends. The hybrid ribozymes can also be modified to increase their ability to penetrate the target tissue by, e.g., coupling them to lipophilic compounds. In addition, hybrid ribozymes can be targeted to particular cells by coupling them to ligands specific for receptors on the cell surface of a target cell. Hybrid ribozymes can also be targeted to specific cell types by being conjugated to monoclonal antibodies that specifically bind to cell-type-specific receptors.

The present hybrid ribozymes can be used in eukaryotic cells ranging from yeast to humans. The ribozymes can be applied, for example, to target ribonucleotides in fungi. For example, the invention can be applied in methods for treating a fungal infection (e.g., *Candida albicans, Blastomyces dermatitidus*, and *Histoplasma capsulatum*), in a patient. In these methods, hybrid ribozymes can be targeted to fungal RNA sequences which, when cleaved, for example, reduce the rate of fungal cell division. For treatment of some of the manifestations of these infections, topical administration may be desired.

For topical administration, a therapeutically effective amount of one or more of the hybrid ribozymes, or expression constructs encoding the hybrid ribozymes, is applied to the desired site on the skin, preferably in combination with a pharmaceutically acceptable carrier, e.g., a spreadable cream, gel, lotion, or ointment, or a liquid such as saline. For use on the skin, the penetration of the nucleic acids into the tissue may be accomplished by a variety of methods known to those of ordinary skill in this field. For example, the hybrid ribozyme expression constructs may be incorporated into a transdermal patch that is applied to the skin. Preferably, the penetration resulting from these methods is enhanced with a chemical transdermal delivery agent such as dimethyl sulfoxide (DMSO) or the nonionic surfactant, n-decylmethyl sulfoxide (NDMS), as described in Choi et al., *Pharmaceutical Res.,* 7(11):1099, 1990. Dosages for a therapeutically effective amount for topical application would be in the range of 100 ng to 10 mg per treated surface area per day.

EXAMPLES

The following experimental data describe, in part, the discovery that forms the basis of the invention. The techniques described herein are meant to illustrate, but not limit, the hybrid ribozymes, expression constructs, and methods of the invention.

Example 1
Functional Map of yeast U3 snoRNA

Mutational analysis of yeast U3 RNA was conducted to obtain a functional map of the snoRNA (FIG. 1A).

The system for the mutational analysis was based on a S. cerevisiae strain JH84 (Hughes, Embo. J., 10:4231–4239, 1991). In this strain, one of two genes encoding U3 RNA (U3B) is disrupted with a LEU2 marker gene, and the second (U3A) is under the control of the GAL1 promoter. Cells grow well on medium containing galactose as a sole carbon source, as U3A RNA is transcribed from the induced GAL1 promoter. In the presence of glucose, the GAL1 promoter is repressed, leading to severe under-accumulation of U3 and subsequent cell death. The lethal condition can be avoided, however, if the cells also contain a plasmid with a functional U3 RNA gene under control of the normal U3 promoter.

To distinguish RNAs expressed from the chromosome and the plasmid, a modified U3 gene with a unique hybridization tag was constructed and designated U3*. The tag was created by switching the sequences of two segments in hairpin 4 of wild type U3. The secondary structure of the hairpin was not altered by creating this tag. Mutation of the plasmid gene and subsequent analysis of cell growth on glucose, and U3* RNA accumulation on galactose makes it possible to test the importance of specific elements for RNA function and production.

Materials and Methods

Yeast transformants initially were grown on plates with solid YNB (0.67% yeast nitrogen base) selective medium containing 2% galactose, and then tested for ability to grow in the same medium supplemented with 5% glucose. For RNA isolation, yeast cells were grown in liquid YNB medium, containing either 2% galactose, or 2% glucose as a carbon source.

E. coli strain DH5α (supE44 lacU169 (φ80 lacz-AM15) hsdR17 recA1 endA1 gyrA96 thi-1 relA1), used for all cloning procedures was grown on either liquid or solid LB (0.5% yeast extract, 1% tryptone, 1% NaCl) medium, supplemented with ampicillin when necessary.

Bacterial and yeast strains were transformed with plasmids using slightly modified versions of the conventional calcium chloride (Hanahan, J. Mol. Biol., 166:557, 1983) and lithium acetate (Rose et al., Methods in Yeast Genetics: A Laboratory Course Manual, 1990) methods, respectively.

Plasmid isolation from E. coli and total RNA isolation from yeasts were performed by a boiling miniprep method (Sambrook et al., supra) and a hot-phenol/glass beads (Kohrer et al., Methods Enzymol., 194:398–405, 1991) method, respectively. Plasmids containing modified U3 sequences were verified by sequencing using the dsDNA Cycle Sequencing System Kit from BRI, Life Technologies, Inc. and appropriate oligonucleotides. Oligonucleotides used for DNA sequencing and probing of U3 RNA were end labeled using ($\gamma$-$^{32}$P) ATP and T4-polynucleotide kinase.

Constructs with modified U3 RNA sequences were prepared as follows. The original U3A gene was isolated from the plasmid pREX4A (kindly provided by J. Hughes) as blunt-ended Hind III fragment, and inserted into the blunt-ended Sal I site of the pBluescript IISK(−) vector (Stratagene) with a removed BstXI site, to generate plasmid pBU3. The construct pBU3* encoding the U3* was prepared, based on this plasmid.

The basic strategies for mutagenesis of the U3 gene are shown in FIGS. 1B–1E. All of the strategies included two steps of polymerase chain reaction ("PCR") amplification. To introduce point mutations or make substitutions of the short sequences, strategies shown on FIGS. 1B and 1C were used. Multiple mutations were created using the strategy shown on FIG. 1D. Substitution or deletions of large regions were made as shown on FIG. 1D. Arrows labeled with numbers represent primers used for PCR. "X" and "Y" represent restriction sites used for subsequent cloning. Open boxes designate wild type sequences, and black boxes designate mutant sequences. PCR was performed using well known techniques.

Plasmids used for yeast transformation were prepared by cloning EcoR I-Xho I fragments carrying mutated U3 RNA genes from the pBU3*-based constructs into shuttle vector pRS313 (Sikorski et al., Genetics, 122:19–27, 1989). The resultant plasmids were pRU3 (wild type U3), pRU3* (C':A-U) (substitution of first A in box C' with T), pRU3* (C'G-C) (substitution of first G in box C with C), pRU3* (C:A-U) (substitution of first A in box C with T), pRU3* (D:A-U) (substitution of last A in box D with T), pRU3* (C:st) (substitution of the whole box C: CGATGA with GCTACT), pRU3* (B:subst) (substitution of the entire box B: GAGTGAG with CTCACTC), pRU3* (Lst:P) (substitution of the terminal stem proximal part: ACTTG with TGGGC), pRU3* (Lst:D) (substitution of the terminal stem distal part: CAAGT with GCCCA), pRU3* (Lst:PD) (substitution of both proximal and distal parts of the terminal stem), pRU3* (c.st:P) [substitution of the central stem proximal part: CCTTTGTAGGG (SEQ ID NO:1) with GGAAACATGGG (SEQ ID NO:2)], pRU3* (c.st:D) (substitution of the central stem distal part: GGGTACAAATCC (SEQ ID NO:3) with CCCATGTTTTCC (SEQ ID NO:4)], pRU3* (c.st:PD) (substitution of both proximal and distal parts of the terminal stem), pRU3* (trunc) (deletion of the region from the 5' end of the RNA up to the proximal part of the terminal stem), pRU3* (del) (deletions of the hairpins 2, 3 and 4). Restriction endonucleases used for treating final PCR fragments before cloning (see FIGS. 1B–1E) were Sal I and BstX I. All new constructs were verified by sequencing of the mutated regions.

Accumulation of RNA transcribed from each of the plasmid construct in yeast cells was analyzed on Northern blots as described previously (Samarsky et al., Nucleic Acids Res., 23:2548–2554, 1995). Briefly, total cellular RNA was extracted, electrophoresed in 8% SDS-polyacrylamide gel, and transferred onto nitrocellulose membrane. Equality of the transferred RNA in each lane on the nitrocellulose membrane was verified by ethidium bromide staining. Oligonucleotides for probing U3 RNA were: (1) C163 (CATAGGATGGGTCAAGATCATCGCGCC; SEQ ID NO:5) which recognizes U3, U3* and all their derivatives; (2) SD14 (GCCGAACCGCTAAGGATTGCGGAC; SEQ ID NO:6), which hybridizes to hairpin 4 in wildtype U3, but not that of U3*; and (3) SD13 (CGGCTTAGGCTAAGCTAAGGCAG; SEQ ID NO:7), which binds to U3* and all its mutant derivatives, but not wild type U3.

Oligonucleotides used for PCR mutagenesis were the following.

(1) All mutations (flanking oligonucleotides):
Universal M13 forward and reverse primers
(New England Biolabs);

(2) U3*: CGGCTTAGGCTAAGCTAAGGCCAGCAAGCTAATTTAGATTCAA (SEQ ID NO:8)
and
CTGGCCTTAGCTTAGCCTAAGCCGCATCTATAATTTTGAATAA; (SEQ ID NO:9)

(3) U3*(C':G-C): CCAACTTGGTTCATGAGTCCC; (SEQ ID NO:10)

(4) U3*(c':A-U): CCAACTTGGTTGTTGAGTCCC; (SEQ ID NO:11)

(5) U3*(C:G-C): GGATGGGTCAAGATCATGGCGCC; (SEQ ID NO:12)

(6) U3*(C:A-U): GGATGGGTCAAGATCAACGCGCC; (SEQ ID NO:13)

(7) U3*(D:A-U): GTGGTTAACTTGACAGACTGCCN; (SEQ ID NO:14)

(8) U3*(t.st:P) and U3*(t.st:PD):
CACTGAATCCATGGGCGTTGATGAGT (SEQ ID NO:15)
and
GACTCATCAACGCCCATGGATTCAGTG; (SEQ ID NO:16)

(9) U3*(t.st:P) and U3*(t.st.PD):
TGGCAGTCTGAGCCCATAACCACTTT (SEQ ID NO:17)
and
AAAGTGGTTATGGGCTCAGACTGCCA; (SEQ ID NO:18)

(10) U3*(c.st:P) and U3*(c.st:PD):
GGAAACATGGGCAGAGTGAGAAACCGAAATTG (SEQ ID NO:19)
and
CGGTTTCTCACTCTGCCCATGTTTCCTTATGGGACTCATCAACCAA; (SEQ ID NO:20)

(11) U3*(c.st:D) and U3*(c.st:PD):
GGTCCCATGTTTTCCCAGTCTGACAAGTTAACCAC (SEQ ID NO:21)
and
CTTGTCAGACTGGGAAAACATGGGACCATAGAGCCCTATCCCTTC; (SEQ ID NO:22)

(12) U3*(trune):
TGACTCTGTCGACAACTTGGTTGATGAGTCCC; (SEQ ID NO:23)
and

(13) U3*(del):
GTGAGAAACCGGCGCGATGATCTTGATGGGTACAAATGGCAGTCTGAC (SEQ ID NO:24)
and
ATCAAGATCATCGCGCCGGTTTCTCACTCTGGGGTAC. (SEQ ID NO:25)

Restriction endonucleases used for treating final PCR fragments before cloning were SalI and BstXI. All new constructs were verified by sequencing of the mutated regions.

Results

Figure 2:
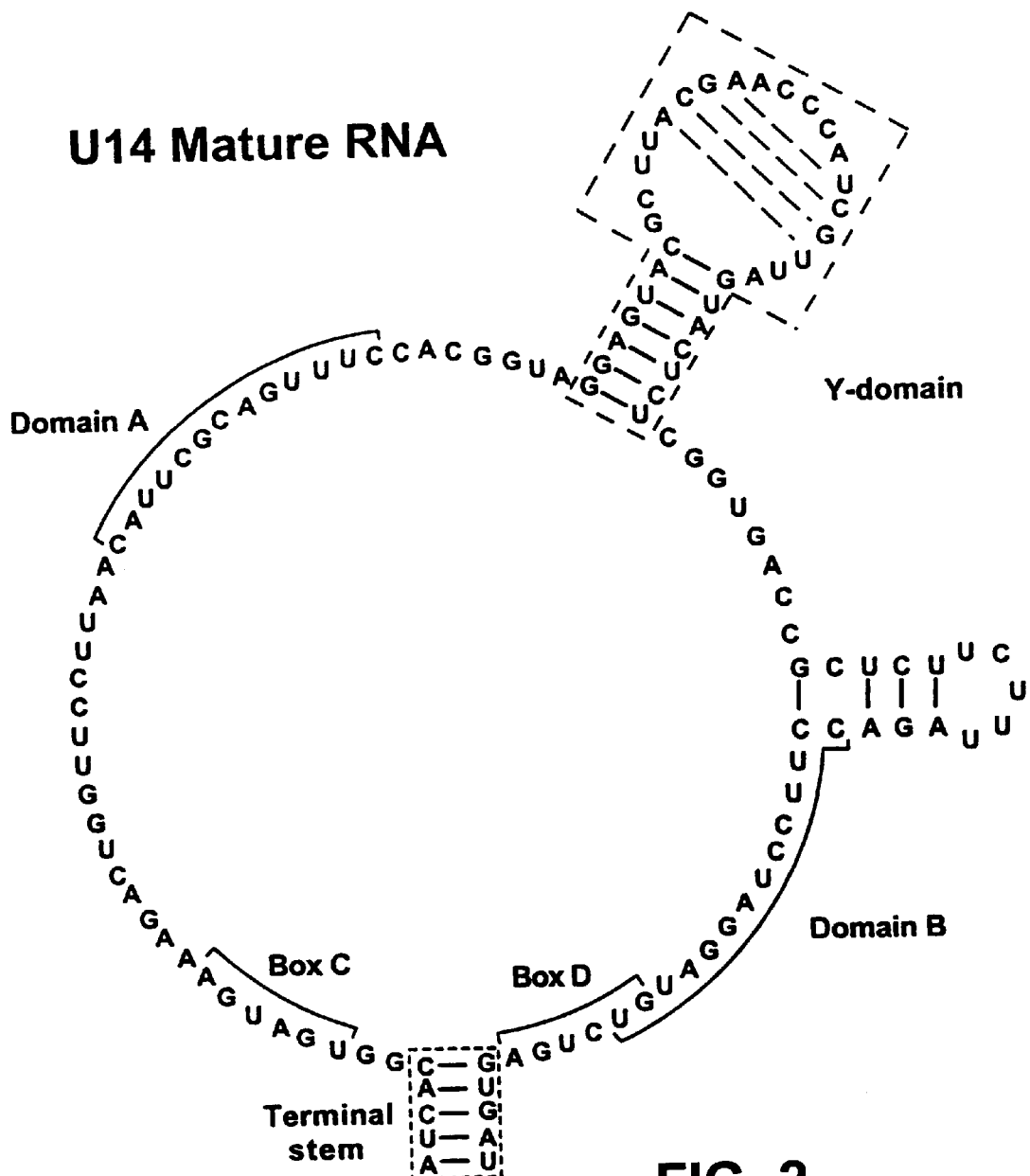
FIG. 2 is a schematic diagram showing the secondary structure of U14 snoRNA (SEQ ID NO:30).

The mutagenesis studies demonstrated that conserved boxes B and C, though important for cell growth, are not essential for U3 production. Nucleotide changes in boxes C' and D, however, led to severe under-accumulation of U3. Mutations in the regions flanking boxes C' and D, which have a potential of forming a short terminal stem, demonstrated the importance of those stems in vivo. Taken together, these data suggest that the U3 box C'/D-stem structure is structurally and functionally homologous to the box C/D-stem motif of the U14 RNA (FIG. 2).

Example 2
U3-Based Hybrid Ribozymes

This example describes cis-acting and trans-acting hybrid ribozymes that were made based on *Saccharomyces cerevisiae* U3 snoRNA. Yeast offers great experimental advantages for ribozyme development, although previous efforts to cleave RNA with ribozymes in this organism were not encouraging.

Materials and Methods

Yeast strain MH2 (a/α ade2-110/ade2-110 his3/his3 trp1-A1/trp1-A1 ura3-52/ura3-52 leu2-3,112/leu2-3,112) was used for transformation with cis-ribozyme expressing constructs. Other yeast strains can also be used to express the new hybrid ribozymes. For trans-ribozyme experiments, MH2a haploid, a MH2 derivative, was used for transformation with constructs encoding target-containing RNAs; and MH2α haploid, also a MH2 derivative, was used for transformation with constructs encoding hybrid ribozyme-containing RNAs.

After crossing of the haploid strains on YEPD medium (supra), diploid strains expressing RNAs of both types were recovered and used for analysis. Media used for yeast cultivation were essentially the same as above. Cloning procedures were performed as described above.

All ribozyme and target expressing constructs were prepared in the context of natural U3 environment (e.g., using the same promoter and terminator). Mutations in U3* or U3del (infra) were created by a simple one step PCR/cloning procedure, as convenient restriction sites Sal I and BstX I were available for cloning at both sides of the PCR product. Mutations in U3* generated either genes expressing RNA hybrids for the cis-ribozyme experiments or for expressing target RNAs for the trans-ribozyme experiments. Mutations in U3del generated genes expressing trans-acting hybrid ribozyme.

Genes in the context of the 1.3 kb Hind III fragments (supra) expressing cis-ribozymes or target sequences were transformed into yeast in the context of low-copy number plasmid pRS313 (Sikorski et al., *Genetics*, 122:19–27, 1989). Ribozyme containing molecules for the trans-ribozyme experiments were expressed either from low-copy number plasmid pRS316 (Sikorski et al., *Genetics*, 122:19–27) or from the derivative of a common high-copy number plasmid YEp24.

In vitro transcription of the RNAs for the cis-ribozyme experiment was conducted according to the protocol of (Gilman et al., *Current Protocols in Molecular Biology*, pp. 4.7.1–4.7.6, 1993), using PCR fragments containing corresponding hybrid sequences and T7 RNA polymerase promoter [$\alpha$-$^{32}$P]UTP (800 Ci/mmol; DuPont NEN) and T7 RNA polymerase. Transcription products were separated in 8% denaturing polyacrylamide gel.

Cis-Acting Hybrid Ribozymes

Figure 3:
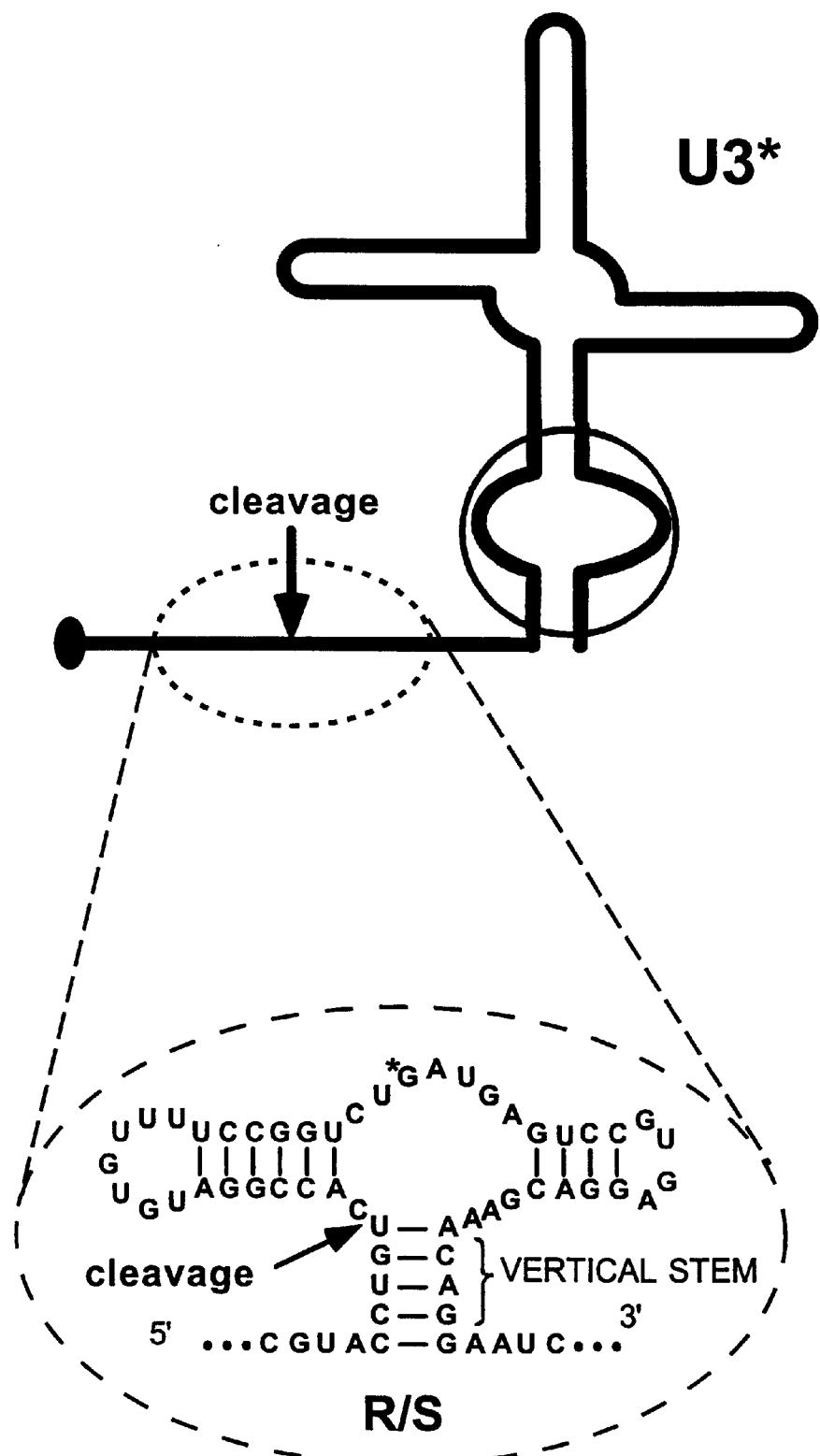
FIG. 3 is a schematic diagram showing a cis-acting U3-based hammerhead hybrid ribozyme (SEQ ID NO:31).

To test the feasibility of generating a hybrid ribozyme using stabilizing sequences from a snoRNA and catalytic sequences from a ribozyme, a sequence corresponding to a classical cis-acting hammerhead ribozyme (52 nucleotides or nt) was inserted into U3*, replacing nucleotides 10–67 in U3*'s 5' region (FIG. 3).

This hybrid ribozyme contained both catalytic ("R") and substrate ("S", i.e., target) sequences. The structure of the hybrid ribozyme is depicted schematically in the upper portion of FIG. 3. The knob at the 5' terminus represents a 5' trimethylguanosine (TMG) cap, which exists in many non-intronic snoRNAs such as U3. The shaded circle at the 3' portion of the hybrid ribozyme represents a protein(s) complexed with the box C'/D-stem motif of U3. The lower panel shows the secondary structure of the inserted hammerhead ribozyme. The C and G nucleotides at the bottom of the vertical stem (see enlarged portion in FIG. 3) of the ribozyme are U3 nucleotides, and correspond to the site of ribozyme insertion. The site of ribozyme-dependent cleavage is marked with an arrow. A construct encoding an inactive hybrid ribozyme R(−)/S was obtained by substituting a G known to be essential for hammerhead cleavage with C (labeled with *).

Figure 4:
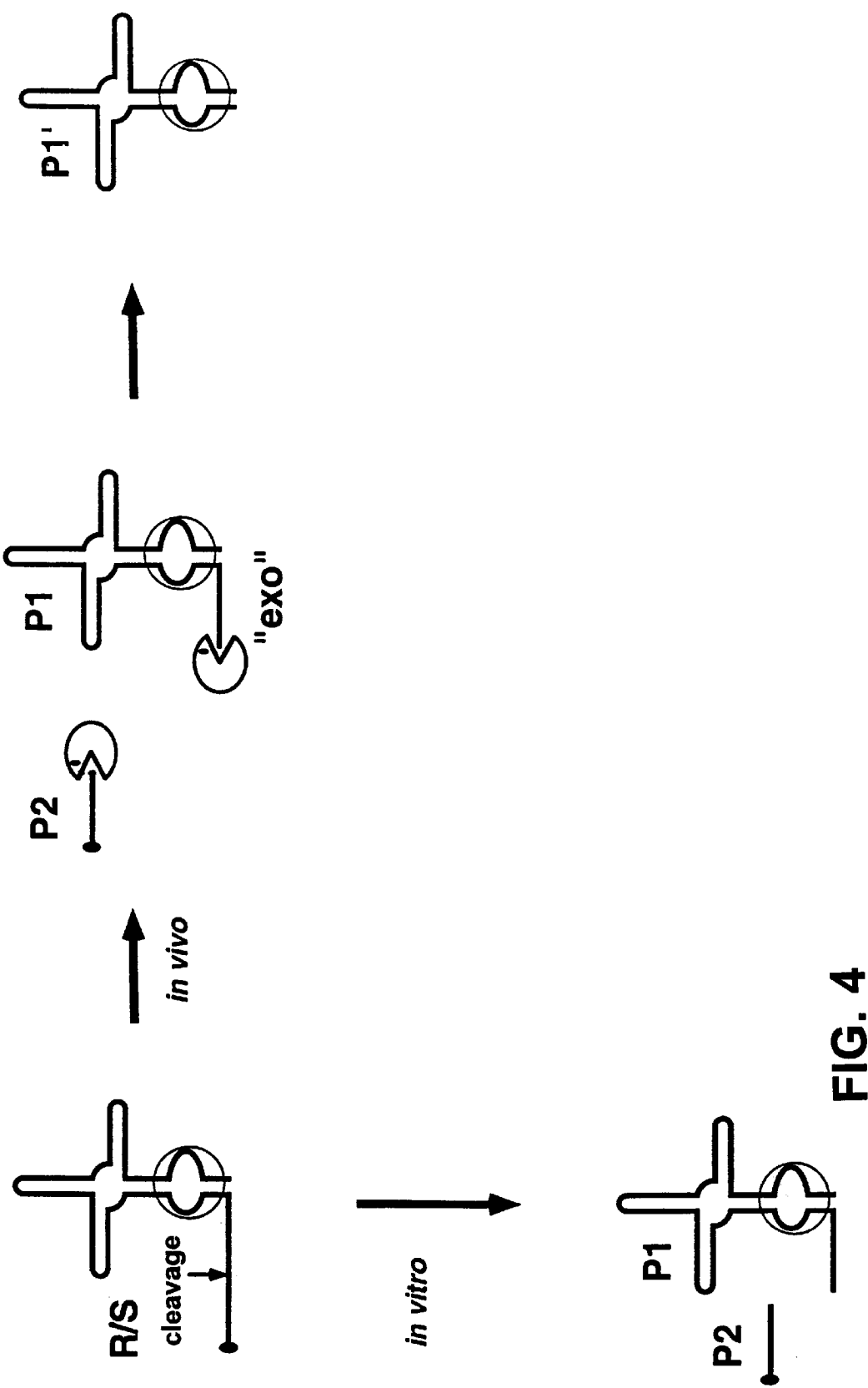
FIG. 4 is a schematic diagram showing the in vivo and in vitro cleavage products of the cis-acting hybrid ribozyme of FIG. 3.

As shown in FIG. 4, the 5' end of a self-cleavage product of the hybrid ribozyme can be degraded by an exonuclease in vivo; thus, in vivo cleavage products can be distinguished from in vitro cleavage products (e.g., those generated during the purification of the hybrid or products) by the former's smaller sizes.

The hybrid ribozyme was introduced into yeast cells by transforming the yeast cells with pRS313-R(+)/S, a DNA construct encoding the active cis hybrid ribozyme. RNAs were subsequently extracted from the cells, electrophoresed on 8% denaturing polyacrylamide gel, and blotted onto nylon membrane. A $^{32}$P end-labeled oligonucleotide probe specific to the genetic tag sequence in U3* was used in hybridization. The RNA amount in each lane was normalized by rehybridizing the membrane with a radioactive oligonucleotide specific to yeast U14 snoRNA.

Northern analysis data revealed that expression of the active cis hybrid ribozyme construct, i.e., pRS313-R(+)/S, in yeast cells resulted in accumulation of the cleaved and trimmed hybrid ribozyme RNA product P1' (FIG. 4). In contrast, expression of the inactive hybrid ribozyme construct, i.e., pRS313-R(−)/S, resulted in production of full length hybrid ribozyme; no cleavage products were observed.

On the other hand, in vitro transcription of pRS313-R (+)/S by T7 RNA polymerase (Promega) resulted in accumulation of the cleaved, but not trimmed hybrid ribozyme molecule P1, whereas transcription of pRS313-R(−)/S construct resulted in only the intact RNA. The results also showed that self-cleavage of the active cis hybrid ribozyme occurred at a high rate in the transcription reaction mix.

To demonstrate that ribozyme-dependent cleavage and subsequent trimming of the R(+)/S hybrid ribozyme in vivo did not occur during the RNA isolation procedure, purification of the in vitro transcribed R(+)/S-U3* and R(−)/S-U3* molecules was performed in parallel with extraction of RNAs from the yeast cells expressing the R(+)/S and R(−)/S molecules. Results obtained from Northern analysis of the resultant RNAs were consistent with the pathways depicted in FIG. 4.

The complete sequence (SEQ ID NO:26) of the R(+)/S-U3* cis hybrid ribozyme is (position marked with * is changed to C in R(−)/S):

GUC GAC GUA CCU GUC ACC GGA UGU GUU UUC CGG UCU

G*AU GAG UCC GUG AGG ACG AAA CAG GAA UCC AAC UUG

GGU UGA UGA GUC CCA UAA CCU UUG UAC CCC AGA GUG

AGA AAC CGA AAU UGA AAU CUA AAU UAG CUU GCU GGC

CUU GGC UUA GCC UAA GCC GCA UCU AUA AUU UUG AAU

AAA AAU UUU GGC CGU UGC AUU UGU AGU UUU UUC CUU

UGG AAG UAA UUA CAA UAU UUU AUG GCG CGA UGA UCU

UGA CCC AUC CUA UGU ACU UCU UUU UGA AGA UAG GGG

CUC UAU GGG UGG GUA CAA AUG GCA GUC UGA CAA GUU

The positive results described above demonstrated that the rationale of our strategy was correct, i.e. that: (1) a stable snoRNA-ribozyme hybrid molecule can be expressed in good abundance in a eukaryotic cell; (2) ribozyme-dependent cleavage in this context can occur with high efficiency; and (3) a stable by-product of the cleavage accumulates faithfully.

Trans-Acting Hybrid Ribozyme

Figure 5:
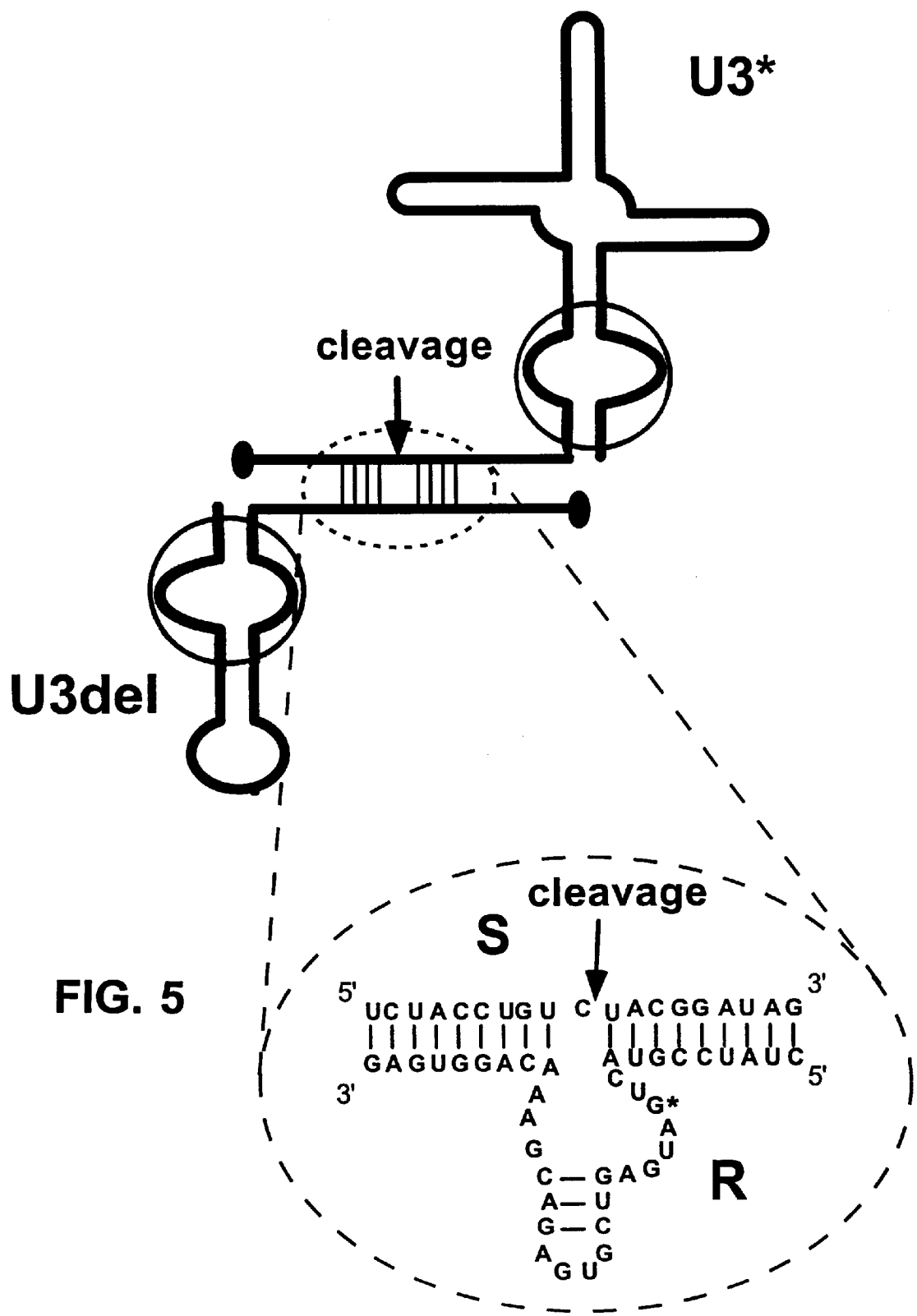
FIG. 5 is a schematic diagram showing a trans-acting U3-based hammerhead hybrid ribozyme (U3del) (SEQ ID NO:33) hybridized to a target sequence inserted into a genetically tagged U3 (i.e., U3*) (SEQ ID NO:32).

The efficiency of in vivo hybrid ribozyme-dependent cleavage was also assessed in the trans configuration. Two DNA constructs were generated: One, pRS313-S-U3*, encoded a U3* RNA with its nucleotides 6–60 substituted by a 19 nucleotide target sequence of a hammerhead ribozyme, and the other, i.e., pRS316-R(+)-U3del, encoded a deletional variant (no hybridization tag) U3 RNA whose nucleotides 6–60 were replaced with a 46 nucleotide hammerhead ribozyme sequence (FIG. 5). This U3 variant did not contain hairpins 2, 3, and 4, so that the substrate- and ribozyme-containing molecules could be readily distinguished. Control experiments were carried out with a construct, i.e., pRS316-R(−)-U3del, encoding an inactive hybrid ribozyme R(−)-U3del where a G nucleotide (marked with *) was substituted with a C.

All of the above three constructs were generated with low-copy-number vectors (i.e., pRS313 or pRS316). To determine if the ribozyme expression level was rate-limiting, the trans hybrid ribozyme was also expressed from a high-copy-number construct Yep24-R(+)-U3del* (active) or Yep24-R(−)-U3del* (inactive).

The interaction predicted for the U3 derivatives containing the target and catalytic sequences is shown in the upper part of FIG. 5. The hammerhead ribozyme structure formed as a result of this interaction is shown in detail in the enlarged dashed oval in the lower part of the figure. The cleavage site is marked with an arrow.

Figure 6:
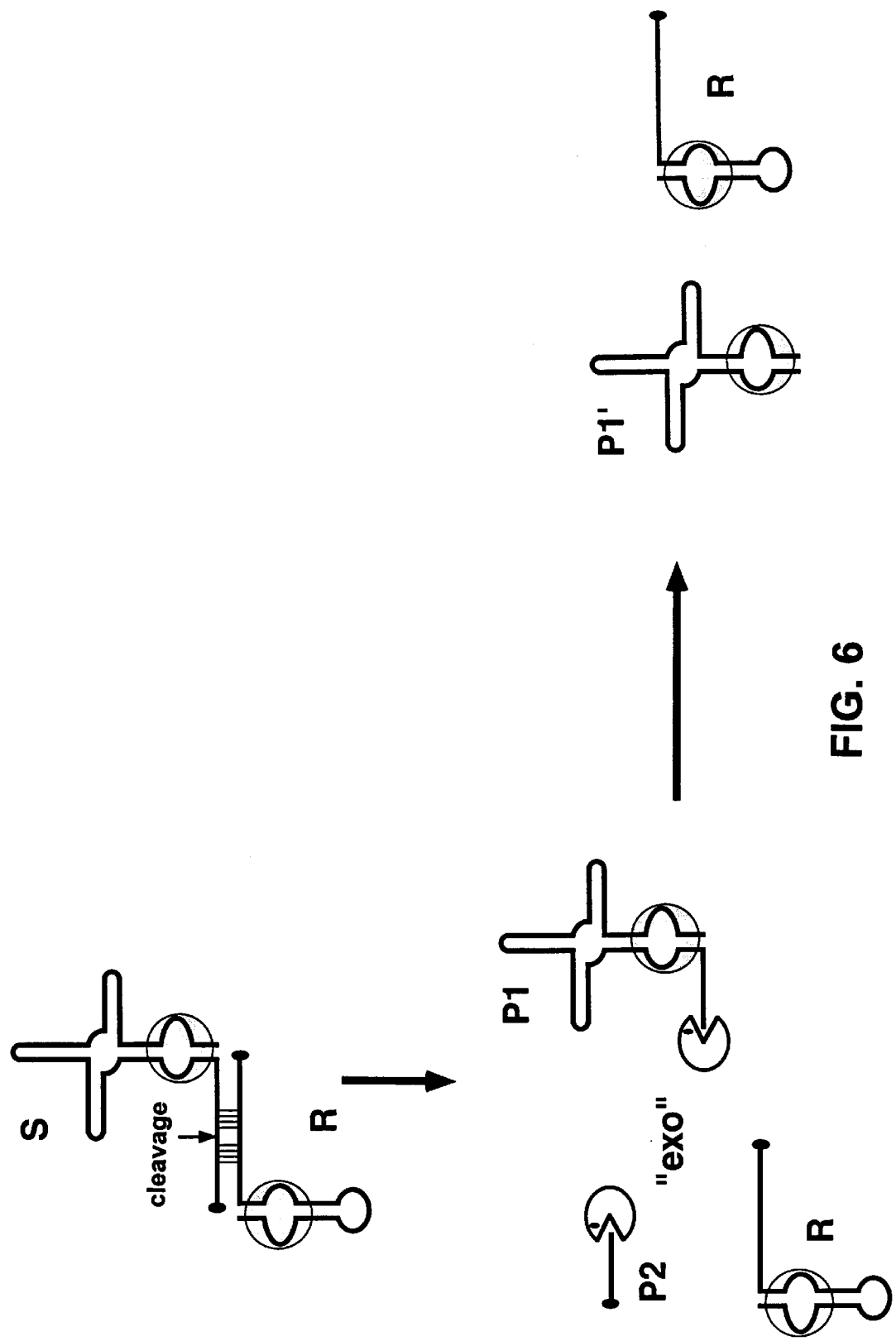
FIG. 6 is a schematic diagram showing the in vivo and in vitro cleavage products of the trans-acting ribozyme of FIG. 5.

The pRS313-S-U3* and one of pRS316-R(+)-U3del, pRS316-R(−)-U3del, Yep24-R(+)-U3del, and Yep24-R(−)-U3del constructs were co-expressed in yeast cells. FIG. 6 depicts the pathway of the trans-cleavage caused by this trans hybrid ribozyme.

Northern blot analysis was performed to identify the RNA products generated by the trans-acting hybrid ribozyme. One of the oligonucleotides used to probe total RNA extracted from the transformed yeast cells specifically hybridized to the genetic tag in S-U3*, the RNA sequence containing a target sequence of the hybrid ribozyme. Another oligonucleotide hybridized specifically to the catalytic sequence of the hybrid ribozyme. The RNA amount in each lane on the gel was normalized with an oligonucleotide probe specific for the endogenous U14 snoRNA.

Expression of S-U3* in the presence of the active ribozyme molecule R(+)-U3del expressed from the low-copy-number pRS316-R(+)-U3del resulted in approximately 60% site-specific cleavage of the full-length molecules. When expressed from the high-copy-number Yep24-R(+)-U3del, R(+)-U3del resulted in more than 95% site-specific cleavage of the full length molecules: To our best knowledge, this is the highest efficiency yet recorded for a trans acting ribozyme in vivo, in any organism.

In contrast, expression of the inactive ribozyme from either the low-copy number low pRS-316-R(−)-U3del, or the high-copy-number Yep24-R(−)-U3del* resulted in barely detectable accumulation of the cleaved S molecule.

Notably, the trans-hybrid ribozyme was expressed at the same level in cells expressing both the hybrid ribozyme and its target and cells expressing the hybrid ribozyme alone. This result indicates that the hybrid ribozyme molecules were not depleted during the cleavage process. Also, active and inactive hybrid ribozymes were expressed at similar levels.

The complete sequence (SEQ ID NO:27) of the R(+)-U3del trans hybrid ribozyme is (position marked with * is changed to C in the inactive hybrid ribozyme R(−)-U3del):

GUC GAC UCA CUA UCC GUA CUG* AUG AGU CCG UGA GGA

CGA AAC AGG UAG ACG UCC ACT GAA UCC AAC UUG GGU

UGA UGA GUC CCA UAA CCU UUG UAC CCC AGA GUG AGA

AAC CGG CGC GAU GAU CUU GUA GGG UAC AAA UGG CAG

UCU GAC AAG UU

The complete sequence (SEQ ID NO:28) of the ribozyme's substrate S-U3* is:

GUC GAC UCU ACC UGU CTA CGG ATA GCC ACT GAA UCC

AAC UUG GGU UGA UGA GUC CCA UAA CCU UUG UAC CCC

AGA GUG AGA AAC CGA AAU UGA AAU CUA AAU UAG CUU

GCU GGC CUU GGC UUA GCC UAA GCC GCA UCU AUA AUU

UUG AAU AAA AAU UUU GGC CGU UGC AUU UGU AGU UUU

UUC CUU UGG AAG UAA UUA CAA UAU UUU AUG GCG CGA

UGA UCU UGA CCC AUC CUA UGU ACU UCU UUU UGA AGA

UAG GGG CUC UAU GGG UGG GUA CAA AUG GCA GUC UGA

CAA GUU

Sequences flanking the trans-ribozyme

The utility of the trans-hybrid ribozyme was further examined with a set of U3*-based substrates. The substrates contained target sequences able to form various numbers of base pairs (bps) with the hybrid ribozyme. The original trans-hybrid ribozyme system allowed formation of 18 bps between the substrate molecule and the hybrid ribozyme molecule: 9 bps in the left arm (L) and 9 bp in the right arm (R) of the ribozyme domain. The new substrates included species with shorter or longer complementarities in the left and right arms.

Figure 7A:
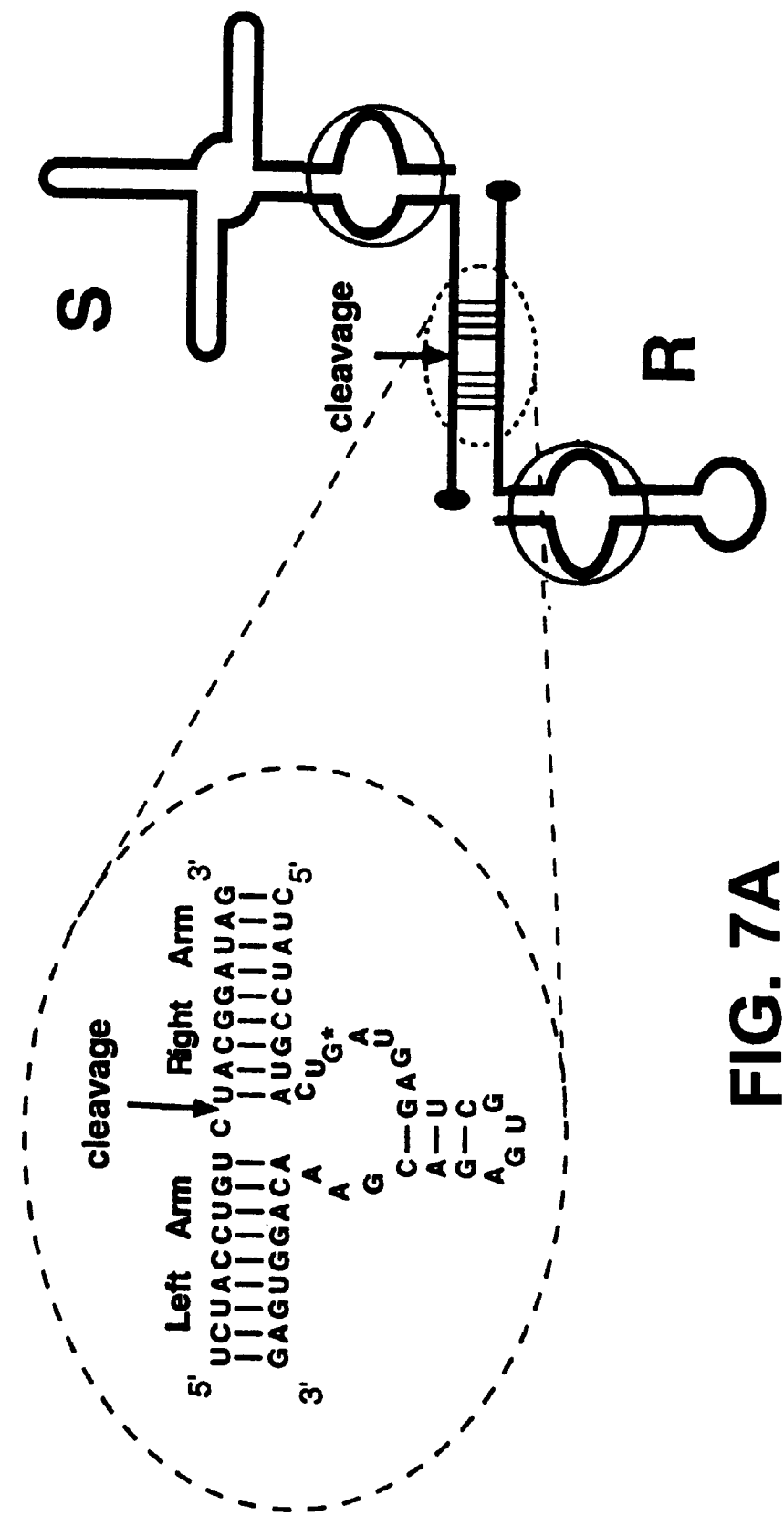
FIG. 7A is a diagram showing the flanking complementarity between the recognition sequences in a trans hybrid ribozyme and a target sequence (see also FIG. 5).
Figure 7B:
FIG. 7B is a Northern blot showing the target-cleaving activity of trans hybrid ribozymes with various recognition arms.

The new ribozyme/substrate pairs are identified by the number of base pairs expected to form with each arm. For example, a substrate able to form 6 bps in the left arm and 9 bps in the right arm is designated 6L:9R. 6L:6R, 6L:9R, 9L:6R, 9L:9R, 12L:12R, and 15L:15R were tested (FIG. 7, where "+", "−", and "v" denote active ribozyme, inactive ribozyme, and vector, respectively). Optimal activity was observed with 9L:6R and 9L:9R, which achieve nearly complete cleavage of a target RNA in living cells.

Other Embodiments

It is to be understood that while the invention has been described in conjunction with the detailed description thereof, that the foregoing description is intended to illustrate and not limit the scope of the invention, which is defined by the scope of the appended claims. For example, the RNA molecules of the invention may contain DNA segments, if desired, to further enhance the stability of the RNA molecules (see, e.g., WO 93/15187).

Other aspects, advantages, and modifications are within the scope of the following claims.

What is claimed is:

1. A recombinant ribonucleic acid (RNA) molecule comprising
   (i) a hammerhead or hairpin ribozyme catalytic sequence; and
   (ii) a small nucleolar RNA (snoRNA) stabilizing motif comprising a box C(C') sequence and a box D sequence;
   wherein the catalytic sequence and the stabilizing motif are arranged to provide the RNA molecule with a three-dimensional configuration in which the catalytic sequence is positioned to cleave a target sequence, and the stabilizing motif adopts a conformation that stabilizes the RNA molecule.

2. The RNA molecule of claim 1, wherein the box C(C') sequence has the sequence DGAHBN, wherein D is U, G, or A; H is U, A, or C; B is G, U, or C; an N is any ribonucleotide.

3. The RNA molecule of claim 1, wherein the box C(C') sequence has the sequence UGAUGA.

4. The RNA molecule of claim 1, wherein the box D sequence has the sequence NYVWGA, where N can be any ribonucleotide; Y is either C or U; V is C, G, or A; and W is U or A.

5. The RNA molecule of claim 1, wherein the box D sequence has the sequence GUCUGA.

6. The RNA molecule of claim 1, further comprising a helical stem, wherein the helical stem comprises a first flanking sequence located adjacent and within four nucleotides of the box C(C') sequence, and a second flanking sequence located adjacent and within four nucleotides of the box D sequence, and wherein the first and second flanking sequences are complementary to each other and each comprise four or more nucleotides.

7. The RNA molecule of claim 6, wherein the first flanking sequence comprises the sequence UUCA, and the second flanking sequence comprises the sequence UGAA, and wherein the first flanking sequence is positioned within two nucleotides of the box C(C') sequence, and the second flanking sequence is positioned within two nucleotides of the box D sequence.

8. The RNA molecule of claim 1, wherein the stabilizing motif further comprises a 5' trimethylguanosine cap.

9. The RNA molecule of claim 1, wherein the target sequence is in a separate molecule.

10. The RNA molecule of claim 9, further comprising a recognition sequence complementary to the target sequence.

11. The RNA molecule of claim 1, further comprising a target sequence positioned within the RNA molecule so that it can be cleaved by the catalytic sequence.

12. The RNA molecule of claim 6, wherein the target sequence is in a separate molecule.

13. The RNA molecule of claim 12, further comprising a recognition sequence complementary to the target sequence.

14. The RNA molecule of claim 13, comprising SEQ ID NO:27.

15. The RNA molecule of claim 6, further comprising a target sequence positioned within the RNA molecule so that it can be cleaved by the catalytic sequence.

16. The RNA molecule of claim 15, comprising SEQ ID NO:26.

17. A eukaryotic expression vector comprising a first nucleic acid sequence encoding the RNA molecule of claim 1.

18. The eukaryotic expression vector of claim 21, further comprising a restriction enzyme site within said first nucleic acid sequence for inserting a second nucleic acid sequence encoding a target sequence, or a sequence complementary thereto, of said catalytic sequence.

19. A composition comprising the eukaryotic expression vector directing expression the RNA molecule of 1.

20. A composition comprising the RNA molecule of claim 10.

21. A method of modulating gene expression in a eukaryotic cell in culture, said method comprising introducing the RNA molecule of claim 10 into the cell.

22. The RNA molecule of claim 1, wherein said motif enables the RNA molecule to localize to the nucleolus of a cell.

23. A recombinant ribonucleic acid (RNA) molecule comprising
   (i) a hammerhead or hairpin ribozyme catalytic sequence; and
   (ii) a small nucleolar RNA (snoRNA) stabilizing motif comprising an ACA box comprising the nucleotide sequence ACA, AUA, or AAA, and an H box comprising the nucleotide sequence ANANNA, wherein N is any nucleotide;
   wherein the catalytic sequence and the stabilizing motif are arranged to provide the RNA molecule with a three-dimensional configuration in which the catalytic sequence is positioned to cleave a target sequence, and the stabilizing motif adopts a conformation that stabilizes the RNA molecule.

24. The RNA molecule of claim 23, wherein the stabilizing motif further comprises a 5' trimethylguanosine cap.

25. The RNA molecule of claim 23, wherein the target sequence is in a separate molecule.

26. The RNA molecule of claim 23, further comprising a target sequence positioned within the RNA molecule so that it can be cleaved by the catalytic sequence.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:1:

CCTTTGTAGG G                                                        11

(2) INFORMATION FOR SEQ ID NO:2:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:2:

GGAAACATGG G                                                        11

(2) INFORMATION FOR SEQ ID NO:3:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:3:

GGGTACAAAT CC                                                       12

(2) INFORMATION FOR SEQ ID NO:4:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:4:

CCCATGTTTT CC                                                       12

(2) INFORMATION FOR SEQ ID NO:5:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:5:

CATAGGATGG GTCAAGATCA TCGCGCC                                             27

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GCCGAACCGC TAAGGATTGC GGAC                                                24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CGGCTTAGGC TAAGCTAAGG CCAG                                                24

(2) INFORMATION FOR SEQ ID NO:8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

CGGCTTAGGC TAAGCTAAGG CCAGCAAGCT AATTTAGATT CAA                           43

(2) INFORMATION FOR SEQ ID NO:9:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

CTGGCCTTAG CTTAGCCTAA GCCGCATCTA TAATTTTGAA TAA                           43

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CCAACTTGGT TCATGAGTCC C                                                   21

(2) INFORMATION FOR SEQ ID NO:11:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:11:

```
CCAACTTGGT TGTTGAGTCC C                                           21
```

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
GGATGGGTCA AGATCATGGC GCC                                         23
```

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
GGATGGGTCA AGATCAACGC GCC                                         23
```

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
GTGGTTAACT TGACAGACTG CCN                                         23
```

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
CACTGAATCC ATGGGCGTTG ATGAGT                                      26
```

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GACTCATCAA CGCCCATGGA TTCAGTG                27

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TGGCAGTCTG AGCCCATAAC CACTTT                 26

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:18:

AAAGTGGTTA TGGGCTCAGA CTGCCA                 26

(2) INFORMATION FOR SEQ ID NO:19:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GGAAACATGG GCAGAGTGAG AAACCGAAAT TG          32

(2) INFORMATION FOR SEQ ID NO:20:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CGGTTTCTCA CTCTGCCCAT GTTTCCTTAT GGGACTCATC AACCAA      46

(2) INFORMATION FOR SEQ ID NO:21:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

GGTCCCATGT TTCCCAGTC TGACAAGTTA ACCAC        35

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

```
CTTGTCAGAC TGGGAAAACA TGGGACCATA GAGCCCTATC CCTTC            45
```

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

```
TGACTCTGTC GACAACTTGG TTGATGAGTC CC                          32
```

(2) INFORMATION FOR SEQ ID NO:24:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

```
GTGAGAAACC GGCGCGATGA TCTTGATGGG TACAAATGGC AGTCTGAC         48
```

(2) INFORMATION FOR SEQ ID NO:25:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

```
ATCAAGATCA TCGCGCCGGT TTCTCACTCT GGGGTAC                     37
```

(2) INFORMATION FOR SEQ ID NO:26:

(i) SEQUENCE CHARACTERISTICS:
        (A) LENGTH: 324 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:26:

```
GUCGACGUAC CUGUCACCGG AUGUGUUUUC CGGUCUGAUG AGUCCGUGAG GACGAAACAG    60

GAAUCCAACU UGGGUUGAUG AGUCCCAUAA CCUUUGUACC CCAGAGUGAG AAACCGAAAU   120

UGAAAUCUAA AUUAGCUUGC UGGCCUUGGC UUAGCCUAAG CCGCAUCUAU AAUUUUGAAU   180

AAAAAUUUUG GCCGUUGCAU UUGUAGUUUU UUCCUUUGGA AGUAAUUACA AUAUUUUAUG   240
```

```
GCGCGAUGAU CUUGACCCAU CCUAUGUACU UCUUUUUGAA GAUAGGGGCU CUAUGGGUGG      300

GUACAAAUGG CAGUCUGACA AGUU                                            324

(2) INFORMATION FOR SEQ ID NO:27:

(i) SEQUENCE CHARACTERISTICS:
         (A) LENGTH: 155 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:27:

GUCGACUCAC UAUCCGUACU GAUGAGUCCG UGAGGACGAA ACAGGUAGAC GUCCACTGAA      60

UCCAACUUGG GUUGAUGAGU CCCAUAACCU UGUACCCCA GAGUGAGAAA CCGGCGCGAU      120

GAUCUUGAUG GGUACAAAUG GCAGUCUGAC AAGUU                                155

(2) INFORMATION FOR SEQ ID NO:28:

(i) SEQUENCE CHARACTERISTICS:
         (A) LENGTH: 294 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:28:

GUCGACUCUA CCUGUCUACG GAUAGCCACT GAAUCCAACU UGGGUUGAUG AGUCCCAUAA      60

CCUUUGUACC CCAGAGUGAG AAACCGAAAU UGAAAUCUAA AUUAGCUUGC UGGCCUUGGC     120

UUAGCCUAAG CCGCAUCUAU AAUUUUGAAU AAAAAUUUUG GCCGUUGCAU UUGUAGUUUU     180

UUCCUUUGGA AGUAAUUACA AUAUUUUAUG GCGCGAUGAU CUUGACCCAU CCUAUGUACU     240

UCUUUUUGAA GAUAGGGGCU CUAUGGGUGG GUACAAAUGG CAGUCUGACA AGUU           294

(2) INFORMATION FOR SEQ ID NO:29:

(i) SEQUENCE CHARACTERISTICS:
         (A) LENGTH: 330 base pairs
         (B) TYPE: nucleic acid
         (C) STRANDEDNESS: single
         (D) TOPOLOGY: linear (ii) MOLECULE TYPE: RNA (xi) SEQUENCE DESCRIPTION: SEQ ID NO:29:

GUCGACGUAC UUCAUAGGAU CAUUUCUAUA GGAAUCGUCA CUCUUUGACU CUUCAAAAGA      60

GCCACUGAAU CCAAACUUGG UUGAUGAGUC CCAUAACCUU UGUACCCCAG AGUGAGAAAC     120

CGAAAUUGAA AUCUAAAUUA GCUUGGUCCG CAAUCCUUAG CGGUUCGGCC AUCUAUAAUU     180

UUGAAUAAAA AUUUUGGCCG UUGCAUUUGU AGUUUUUUCC UUUGGAAGUA AUUACAAUAU     240

UUUAUGGCGC GAUGAUCUUG ACCCAUCCUA UGUACUUCUU UUUGAAGGGA UAGGGCUCUA     300

UGGGUGGGUA CAAAUGGCAG UCUGACAAGU                                      330

(2) INFORMATION FOR SEQ ID NO:30:

(i) SEQUENCE CHARACTERISTICS:
         (A) LENGTH: 126 base pairs
         (B) TYPE: nucleic acid
         (C) STRANDEDNESS: single
         (D) TOPOLOGY: linear
```

(ii) MOLECULE TYPE: RNA (xi) SEQUENCE DESCRIPTION: SEQ ID NO:30:

AUCACGGUGA UGAAAGACUG GUUCCUUAAC AUUCGCAGUU UCCACGGUAG GAGUACGCUU    60

ACGAACCCAU CGUUAGUACU CUCGGUGACC GCUCUUCUUU AGACCUUCCU AGGAUGUCUG    120

AGUGAU    126

(2) INFORMATION FOR SEQ ID NO:31:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: RNA (xi) SEQUENCE DESCRIPTION: SEQ ID NO:31:

CGUACCUGUC ACCGGAUGUG UUUUCCGGUC UGAUGAGUCC GUGAGGACGA AACAGGAAUC    60

(2) INFORMATION FOR SEQ ID NO:32:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: RNA (xi) SEQUENCE DESCRIPTION: SEQ ID NO:32:

UCUACCUGUC UACGGAUAG    19

(2) INFORMATION FOR SEQ ID NO:33:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (ii) MOLECULE TYPE: RNA (xi) SEQUENCE DESCRIPTION: SEQ ID NO:33:

GAGUGGACAA AGCAGAGUGC UGAGUAGUCA UGCCUAUC    38